(12) United States Patent
Swartjes et al.

(10) Patent No.: US 12,186,472 B2
(45) Date of Patent: Jan. 7, 2025

(54) BLOOD TREATMENT DEVICE COMPRISING ALKALINE PHOSPHATASE

(71) Applicant: GAMBRO LUNDIA AB, Lund (SE)

(72) Inventors: Jan Swartjes, Tubingen (DE); Markus Storr, Filderstadt (DE); Martin Rempfer, Gomaringen (DE); Isabelle Litzinger, Hechingen (DE); Stefanie Votteler, Reutlingen (DE); Philipp Kuhn, Tubingen (DE)

(73) Assignee: GAMBRO LUNDIA AB, Lund (SE)

( * ) Notice: Subject to any disclaimer, the term of this patent is extended or adjusted under 35 U.S.C. 154(b) by 564 days.

(21) Appl. No.: 17/433,761

(22) PCT Filed: Mar. 6, 2020

(86) PCT No.: PCT/EP2020/055977
§ 371 (c)(1),
(2) Date: Aug. 25, 2021

(87) PCT Pub. No.: WO2020/178420
PCT Pub. Date: Sep. 10, 2020

(65) Prior Publication Data
US 2022/0241484 A1     Aug. 4, 2022

(30) Foreign Application Priority Data
Mar. 6, 2019 (EP) ..................... 19161050

(51) Int. Cl.
*A61M 1/36*     (2006.01)
*A61M 1/16*     (2006.01)
(Continued)

(52) U.S. Cl.
CPC ............ *A61M 1/3687* (2013.01); *A61M 1/16* (2013.01); *A61M 1/3486* (2014.02);
(Continued)

(58) Field of Classification Search
CPC ...... A61M 1/16; A61M 1/348; A61M 1/3679; A61M 1/3687; B01D 63/031;
(Continued)

(56) References Cited

U.S. PATENT DOCUMENTS 6,290,952 B1     9/2001    Poelstra et al.

FOREIGN PATENT DOCUMENTS

| CA | 2167409 A1 | 1/1995 |
|---|---|---|
| WO | 9502326 A1 | 1/1995 |
| WO | WO199955828 | 11/1999 |
| WO | 0196571 A2 | 12/2001 |

(Continued)

OTHER PUBLICATIONS

Machine English translation copy of WO 99/55828 A1 (1999).*
(Continued)

*Primary Examiner* — John Kim
(74) *Attorney, Agent, or Firm* — Barnes & Thornburg LLP

(57) ABSTRACT

The invention relates to a blood treatment device configured to dephosphorylate extracellular adenosine triphosphate (ATP), adenosine diphosphate (ADP), adenosine monophosphate (AMP) and/or lipopolysaccharide (LPS) in the blood of a patient in need thereof in an extracorporeal blood circuit, wherein the device comprises a matrix having alkaline phosphatase (AP) immobilized thereon. The invention further relates to an extracorporeal blood circuit comprising a blood treatment device of the invention and to the blood treatment device for use as a medicament or to methods of treating an infection, preferably a blood or systemic infection, such as sepsis, and/or for the treatment of sepsis-associated acute kidney injury (AKI).

20 Claims, 8 Drawing Sheets

Specification includes a Sequence Listing.

(51) Int. Cl.
    *A61M 1/34*     (2006.01)
    *B01D 63/02*     (2006.01)
    *B01D 69/14*     (2006.01)
    *B01D 71/38*     (2006.01)
    *B01D 71/42*     (2006.01)
    *B01D 71/68*     (2006.01)
    *B01D 71/76*     (2006.01)
    *B01J 31/00*     (2006.01)

(52) U.S. Cl.
    CPC ......... *A61M 1/3679* (2013.01); *B01D 63/031* (2022.08); *B01D 63/034* (2022.08); *B01D 69/148* (2013.01); *B01D 71/383* (2022.08); *B01D 71/421* (2022.08); *B01D 71/68* (2013.01); *B01D 71/76* (2013.01); *B01J 31/003* (2013.01); *B01D 2323/21825* (2022.08); *B01D 2323/2187* (2022.08)

(58) Field of Classification Search
    CPC .. B01D 63/034; B01D 69/148; B01D 71/383; B01D 71/421; B01D 71/68; B01D 71/76; B01D 2323/21825; B01D 2323/2187; B01J 31/003
    See application file for complete search history.

(56) References Cited

FOREIGN PATENT DOCUMENTS

| | | | |
|---|---|---|---|
| WO | 2009064497 | A1 | 5/2009 |
| WO | 2010147642 | A1 | 12/2010 |
| WO | 2018231722 | A1 | 12/2018 |

OTHER PUBLICATIONS

Tihan et al., "Alkaline Phosphatase Immobilization on New Chitosan Membranes with Mg2+ for Biomedical Applications," Marine Drugs, 2018, vol. 16, Issue: 8, Article 287, pp. 1-14.
Rim, Hark et al., "Phosphate Removal by Different Dialysis Modalities," Keimyung Med J, 2006, vol. 25, No. 2, pp. 118-124.
English Translation of Chinese Office Action issued for Application No. 2020800186095, mailed Feb. 1, 2024.
PCT Search Report and Written Opinion prepared for PCT/EP2020/055977, completed May 12, 2020.
Chelpanova, T. I., et al.; "Alkaline Phosphatase Immobilization on Spherical Pectin Gel Particles;" 2016; Applied Biochemistry and Microbiology; vol. 52; Nr. 1; pp. 36-42.
Buts, Jean-Paul, et al.; "Saccharomyces Boulardii Produces in Rat Small Intestine a Novel Protein Phosphatase that inhibits *Escherichia coli* Endotoxin by Dephosphorylation;" 2006; Pediatr. Res., No. 60; pp. 24-29.

* cited by examiner

A

| Membrane | +/- EDC | Weight (mg) | Activity (μmol pNPP/min) | Whole dialyzer (20 g) |
|---|---|---|---|---|
| | | | | (μmol pNPP/min) |
| Chitosan | + | 2,20 | 0,06 | 564 |
| Maleic anhydride | + | 3,50 | 0,10 | 565 |
| Control (PES/PVP) | + | 4,20 | 0,01 | 26 |

B (A)

(B)

(A)

Epoxy resin — Covalently immobilized target protein (B)

Amino resin

Covalently immobilized target protein

SEQUENCE LISTING

<160> NUMBER OF SEQ ID NOS: 6

<210> SEQ ID NO 1
<211> LENGTH: 533
<212> TYPE: PRT

<213> ORGANISM: Bos taurus

<400> SEQUENCE: 1

```
Met Gln Gly Ala Cys Val Leu Leu Leu Gly Leu His Leu Gln Leu
1               5                   10                  15

Ser Leu Gly Leu Val Pro Val Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Arg Thr
        115                 120                 125

Ile Gly Val Ser Ala Ala Arg Tyr Asn Gln Cys Lys Thr Thr Arg
130                 135                 140

Gly Asn Glu Val Thr Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Met Asn Gly Cys Gln Asp Ile Ala Ala Gln
        195                 200                 205

Leu Val Asn Asn Met Asp Ile Asp Val Ile Leu Gly Gly Gly Arg Lys
210                 215                 220

Tyr Met Phe Pro Val Gly Thr Pro Asp Pro Glu Tyr Pro Asp Asp Ala
225                 230                 235                 240

Ser Val Asn Gly Val Arg Lys Arg Lys Gln Asn Leu Val Gln Ala Trp
                245                 250                 255

Gln Ala Lys His Gln Gly Ala Gln Tyr Val Trp Asn Arg Thr Ala Leu
            260                 265                 270

Leu Gln Ala Ala Asp Asp Ser Ser Val Thr His Leu Met Gly Leu Phe
        275                 280                 285

Glu Pro Ala Asp Met Lys Tyr Asn Val Gln Gln Asp His Thr Lys Asp
    290                 295                 300

Pro Thr Leu Gln Glu Met Thr Glu Val Ala Leu Arg Val Val Ser Arg
305                 310                 315                 320

Asn Pro Arg Gly Phe Tyr Leu Phe Val Glu Gly Gly Arg Ile Asp His
                325                 330                 335

Gly His His Asp Asp Lys Ala Tyr Met Ala Leu Thr Glu Ala Gly Met
            340                 345                 350

Phe Asp Asn Ala Ile Ala Lys Ala Asn Glu Leu Thr Ser Glu Leu Asp
        355                 360                 365

Thr Leu Ile Leu Val Thr Ala Asp His Ser His Val Phe Ser Phe Gly
    370                 375                 380

Gly Tyr Thr Leu Arg Gly Thr Ser Ile Phe Gly Leu Ala Pro Ser Lys
385                 390                 395                 400
```

-continued

```
Ala Leu Asp Ser Lys Ser Tyr Thr Ser Ile Leu Tyr Gly Asn Gly Pro
                405                 410                 415

Gly Tyr Ala Leu Gly Gly Gly Ser Arg Pro Asp Val Asn Asp Ser Thr
            420                 425                 430

Ser Glu Asp Pro Ser Tyr Gln Gln Gln Ala Ala Val Pro Gln Ala Ser
        435                 440                 445

Glu Thr His Gly Gly Glu Asp Val Ala Val Phe Ala Arg Gly Pro Gln
    450                 455                 460

Ala His Leu Val His Gly Val Glu Glu Glu Thr Phe Val Ala His Ile
465                 470                 475                 480

Met Ala Phe Ala Gly Cys Val Glu Pro Tyr Thr Asp Cys Asn Leu Pro
                485                 490                 495

Ala Pro Thr Thr Ala Thr Ser Ile Pro Asp Ala Ala His Leu Ala Ala
            500                 505                 510

Ser Pro Pro Pro Leu Ala Leu Leu Ala Gly Ala Met Leu Leu Leu Leu
        515                 520                 525

Ala Pro Thr Leu Tyr
    530

<210> SEQ ID NO 2
<211> LENGTH: 532
<212> TYPE: PRT
<213> ORGANISM: Homo sapiens

<400> SEQUENCE: 2

Met Gln Gly Pro Trp Val Leu Leu Leu Leu Gly Leu Arg Leu Gln Leu
1               5                   10                  15

Ser Leu Gly Ile Ile Pro Val Glu Glu Glu Asn Pro Asp Phe Trp Asn
            20                  25                  30

Arg Gln Ala Ala Glu Ala Leu Gly Ala Ala Lys Lys Leu Gln Pro Ala
        35                  40                  45

Gln Thr Ala Ala Lys Asn Leu Ile Ile Phe Leu Gly Asp Gly Met Gly
    50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Asp Asp Tyr
225                 230                 235                 240
```

Ser Gln Gly Gly Thr Arg Leu Asp Gly Lys Asn Leu Val Gln Glu Trp
            245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
            275                 280                 285

Glu Pro Gly Asp Met Lys Tyr Glu Ile His Arg Asp Ser Thr Leu Asp
290                 295                 300

Pro Ser Leu Met Glu Met Thr Glu Ala Ala Leu Leu Leu Leu Ser Arg
305                 310                 315                 320

Asn Pro Arg Gly Phe Phe Leu Phe Val Glu Gly Gly Arg Ile Asp His
            325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
            355                 360                 365

Thr Leu Ser Leu Val Thr Ala Asp His Ser His Val Phe Ser Phe Gly
        370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
            435                 440                 445

Glu Thr His Ala Gly Glu Asp Val Ala Val Phe Ala Arg Gly Pro Gln
        450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Leu Gly Thr
            515                 520                 525

Ala Thr Ala Pro
530

<210> SEQ ID NO 3
<211> LENGTH: 524
<212> TYPE: PRT
<213> ORGANISM: Homo sapiens

<400> SEQUENCE: 3

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn

```
                65                  70                  75                  80
        Pro Gly Glu Glu Thr Arg Leu Glu Met Asp Lys Phe Pro Phe Val Ala
                            85                  90                  95

Leu Ser Lys Thr Tyr Asn Thr Asn Ala Gln Val Pro Asp Ser Ala Gly
                        100                 105                 110

Thr Ala Thr Ala Tyr Leu Cys Gly Val Lys Ala Asn Glu Gly Thr Val
                    115                 120                 125

Gly Val Ser Ala Ala Thr Glu Arg Ser Arg Cys Asn Thr Thr Gln Gly
        130                 135                 140

Asn Glu Val Thr Ser Ile Leu Arg Trp Ala Lys Asp Ala Gly Lys Ser
        145                 150                 155                 160

Val Gly Ile Val Thr Thr Thr Arg Val Asn His Ala Thr Pro Ser Ala
                        165                 170                 175

Ala Tyr Ala His Ser Ala Asp Arg Asp Trp Tyr Ser Asp Asn Glu Met
                    180                 185                 190

Pro Pro Glu Ala Leu Ser Gln Gly Cys Lys Asp Ile Ala Tyr Gln Leu
                195                 200                 205

Met His Asn Ile Arg Asp Ile Asp Val Ile Met Gly Gly Gly Arg Lys
        210                 215                 220

Tyr Met Tyr Pro Lys Asn Lys Thr Asp Val Glu Tyr Glu Ser Asp Glu
        225                 230                 235                 240

Lys Ala Arg Gly Thr Arg Leu Asp Gly Leu Asp Leu Val Asp Thr Trp
                        245                 250                 255

Lys Ser Phe Lys Pro Arg Tyr Lys His Ser His Phe Ile Trp Asn Arg
                    260                 265                 270

Thr Glu Leu Leu Thr Leu Asp Pro His Asn Val Asp Tyr Leu Leu Gly
                275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
        305                 310                 315                 320

Arg Lys Asn Pro Lys Gly Phe Phe Leu Leu Val Glu Gly Gly Arg Ile
                        325                 330                 335

Asp His Gly His His Glu Gly Lys Ala Lys Gln Ala Leu His Glu Ala
                    340                 345                 350

Val Glu Met Asp Arg Ala Ile Gly Gln Ala Gly Ser Leu Thr Ser Ser
                355                 360                 365

Glu Asp Thr Leu Thr Val Val Thr Ala Asp His Ser His Val Phe Thr
        370                 375                 380

Phe Gly Gly Tyr Thr Pro Arg Gly Asn Ser Ile Phe Gly Leu Ala Pro
        385                 390                 395                 400

Met Leu Ser Asp Thr Asp Lys Lys Pro Phe Thr Ala Ile Leu Tyr Gly
                        405                 410                 415

Asn Gly Pro Gly Tyr Lys Val Val Gly Gly Glu Arg Glu Asn Val Ser
                    420                 425                 430

Met Val Asp Tyr Ala His Asn Asn Tyr Gln Ala Gln Ser Ala Val Pro
                435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
        465                 470                 475                 480

Pro His Val Met Ala Tyr Ala Ala Cys Ile Gly Ala Asn Leu Gly His
                        485                 490                 495
```

```
Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 4
<211> LENGTH: 528
<212> TYPE: PRT
<213> ORGANISM: Homo sapiens

<400> SEQUENCE: 4

Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
                20                  25                  30

Arg Gln Ala Ala Glu Ala Leu Asp Ala Ala Lys Lys Leu Gln Pro Ile
                35                  40                  45

Gln Lys Val Ala Lys Asn Leu Ile Leu Phe Leu Gly Asp Gly Leu Gly
            50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
                100                 105                 110

Ala Thr Ala Thr Ala Tyr Leu Cys Gly Val Lys Ala Asn Phe Gln Thr
            115                 120                 125

Ile Gly Leu Ser Ala Ala Ala Arg Phe Asn Gln Cys Asn Thr Thr Arg
130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
                180                 185                 190

Met Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Gly Arg Lys
210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
                260                 265                 270

Met Gln Ala Ser Leu Asp Gln Ser Val Thr His Leu Met Gly Leu Phe
            275                 280                 285

Glu Pro Gly Asp Thr Lys Tyr Glu Ile His Arg Asp Pro Thr Leu Asp
290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
```

```
            340                 345                 350
Phe Asp Asp Ala Ile Glu Arg Ala Gly Gln Leu Thr Ser Glu Glu Asp
        355                 360                 365

Thr Leu Thr Leu Val Thr Ala Asp His Ser His Val Phe Ser Phe Gly
    370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Gln Ala Ala Val Pro Leu Ser Ser
        435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
        515                 520                 525

<210> SEQ ID NO 5
<211> LENGTH: 509
<212> TYPE: PRT
<213> ORGANISM: Homo sapiens

<400> SEQUENCE: 5

Val Ile Pro Ala Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
            20                  25                  30

Ala Lys Asn Leu Ile Leu Phe Leu Gly Asp Gly Leu Gly Val Pro Thr
        35                  40                  45

Val Thr Ala Thr Arg Ile Leu Lys Gly Gln Lys Asn Gly Lys Leu Gly
    50                  55                  60

Pro Glu Thr Pro Leu Ala Met Asp Arg Phe Pro Tyr Leu Ala Leu Ser
65                  70                  75                  80

Lys Thr Tyr Asn Val Asp Arg Gln Val Pro Asp Ser Ala Ala Thr Ala
                85                  90                  95

Thr Ala Tyr Leu Cys Gly Val Lys Ala Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Gln Ala Gly Lys Ser Val Gly
    130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190
```

```
Asn Met Asp Ile Asp Val Ile Leu Gly Gly Arg Lys Tyr Met Phe
            195                 200                 205

Pro Met Gly Thr Pro Asp Pro Glu Tyr Pro Ala Asp Ala Ser Gln Asn
210                 215                 220

Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
                245                 250                 255

Ser Leu Asp Gln Ser Val Thr His Leu Met Gly Leu Phe Glu Pro Gly
            260                 265                 270

Asp Thr Lys Tyr Glu Ile His Arg Asp Pro Thr Leu Asp Pro Ser Leu
        275                 280                 285

Met Glu Met Thr Glu Ala Ala Leu Arg Leu Leu Ser Arg Asn Pro Arg
    290                 295                 300

Gly Phe Tyr Leu Phe Val Glu Gly Gly Arg Ile Asp His Gly His His
305                 310                 315                 320

Glu Gly Val Ala Tyr Gln Ala Leu Thr Glu Ala Val Met Phe Asp Asp
                325                 330                 335

Ala Ile Glu Arg Ala Gly Gln Leu Thr Ser Glu Glu Asp Thr Leu Thr
            340                 345                 350

Leu Val Thr Ala Asp His Ser His Val Phe Ser Phe Gly Gly Tyr Thr
        355                 360                 365

Leu Arg Gly Ser Ser Ile Phe Gly Leu Ala Pro Ser Lys Ala Gln Asp
    370                 375                 380

Ser Lys Ala Tyr Thr Ser Ile Leu Tyr Gly Asn Gly Pro Gly Tyr Val
385                 390                 395                 400

Phe Asn Ser Gly Val Arg Pro Asp Val Asn Glu Ser Glu Ser Gly Ser
                405                 410                 415

Pro Asp Tyr Gln Gln Gln Ala Ala Val Pro Leu Ser Ser Glu Thr His
            420                 425                 430

Gly Gly Glu Asp Val Ala Val Phe Ala Arg Gly Pro Gln Ala His Leu
        435                 440                 445

Val His Gly Val Gln Glu Gln Ser Phe Val Ala His Val Met Ala Phe
    450                 455                 460

Ala Ala Cys Leu Glu Pro Tyr Thr Ala Cys Asp Leu Ala Pro Pro Ala
465                 470                 475                 480

Cys Thr Thr Asp Ala Ala His Pro Val Ala Ala Ser Leu Pro Leu Leu
                485                 490                 495

Ala Gly Thr Leu Leu Leu Gly Ala Ser Ala Ala Pro
            500                 505

<210> SEQ ID NO 6
<211> LENGTH: 484
<212> TYPE: PRT
<213> ORGANISM: Artificial Sequence
<220> FEATURE:
<223> OTHER INFORMATION: Recombinant AP

<400> SEQUENCE: 6

Val Ile Pro Ala Glu Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
            20                  25                  30

Ala Lys Asn Leu Ile Leu Phe Leu Gly Asp Gly Leu Gly Val Pro Thr
        35                  40                  45
```

-continued

```
Val Thr Ala Thr Arg Ile Leu Lys Gly Gln Lys Asn Gly Lys Leu Gly
 50                  55                  60
Pro Glu Thr Pro Leu Ala Met Asp Arg Phe Pro Tyr Leu Ala Leu Ser
 65                      70                  75                  80
Lys Thr Tyr Asn Val Asp Arg Gln Val Pro Asp Ser Ala Ala Thr Ala
                 85                  90                  95
Thr Ala Tyr Leu Cys Gly Val Lys Ala Asn Phe Gln Thr Ile Gly Leu
            100                 105                 110
Ser Ala Ala Arg Phe Asn Gln Cys Asn Thr Thr Arg Gly Asn Glu
        115                 120                 125
Val Ile Ser Val Met Asn Arg Ala Lys Gln Ala Gly Lys Ser Val Gly
130                 135                 140
Val Val Thr Thr Thr Arg Val Gln His Ala Ser Pro Ala Gly Thr Tyr
145                 150                 155                 160
Ala His Thr Val Asn Arg Asn Trp Tyr Ser Asp Ala Asp Met Pro Ala
                165                 170                 175
Ser Ala Arg Gln Glu Gly Cys Gln Asp Ile Ala Thr Gln Leu Ile Ser
        180                 185                 190
Asn Met Asp Ile Asp Val Ile Leu Gly Gly Gly Arg Lys Tyr Met Phe
    195                 200                 205
Pro Met Gly Thr Pro Asp Pro Glu Tyr Pro Ala Asp Ala Ser Gln Asn
210                 215                 220
Gly Ile Arg Leu Asp Gly Lys Asn Leu Val Gln Glu Trp Leu Ala Lys
225                 230                 235                 240
His Gln Gly Ala Trp Tyr Val Trp Asn Arg Thr Glu Leu Met Gln Ala
                245                 250                 255
Ser Leu Asp Gln Ser Val Thr His Leu Met Gly Leu Phe Glu Pro Gly
        260                 265                 270
Asp Thr Lys Tyr Glu Ile His Arg Asp Pro Thr Leu Asp Pro Ser Leu
    275                 280                 285
Met Glu Met Thr Glu Ala Ala Leu Arg Leu Leu Ser Arg Asn Pro Arg
290                 295                 300
Gly Phe Tyr Leu Phe Val Glu Gly Gly Arg Ile Asp His Gly His His
305                 310                 315                 320
Glu Gly Val Ala Tyr Gln Ala Leu Thr Glu Ala Val Met Phe Asp Asp
                325                 330                 335
Ala Ile Glu Arg Ala Gly Gln Leu Thr Ser Glu Glu Asp Thr Leu Thr
        340                 345                 350
Leu Val Thr Ala Asp His Ser His Val Phe Ser Phe Gly Gly Tyr Pro
    355                 360                 365
Leu Arg Gly Ser Ser Ile Phe Gly Leu Ala Pro Gly Lys Ala Arg Asp
370                 375                 380
Arg Lys Ala Tyr Thr Val Leu Leu Tyr Gly Asn Gly Pro Gly Tyr Val
385                 390                 395                 400
Leu Lys Asp Gly Ala Arg Pro Asp Val Thr Glu Ser Glu Ser Gly Ser
                405                 410                 415
Pro Glu Tyr Arg Gln Gln Ser Ala Val Pro Leu Asp Glu Glu Thr His
        420                 425                 430
Gly Gly Glu Asp Val Ala Val Phe Ala Arg Gly Pro Gln Ala His Leu
    435                 440                 445
```

```
Val His Gly Val Gln Glu Gln Ser Phe Val Ala His Val Met Ala Phe
    450                 455                 460

Ala Ala Cys Leu Glu Pro Tyr Thr Ala Cys Asp Leu Ala Pro Pro Ala
465                 470                 475                 480

Cys Thr Thr Asp
```

BLOOD TREATMENT DEVICE COMPRISING ALKALINE PHOSPHATASE

The invention relates to the field of extracorporeal treatment of the blood of a patient and related hemofilter and adsorber cartridge devices. In particular, the invention relates to alkaline phosphatase (AP) assisted continuous renal replacement therapy (APA-CRRT) to treat sepsis or sepsis-associated acute kidney injury (AKI).

The invention therefore relates to a blood treatment device configured to dephosphorylate extracellular adenosine triphosphate (ATP), adenosine diphosphate (ADP), adenosine monophosphate (AMP) and/or lipopolysaccharide (LPS) in the blood of a patient in need thereof in an extracorporeal blood circuit, wherein the device comprises a matrix having alkaline phosphatase (AP) immobilized thereon. The invention further relates to an extracorporeal blood circuit comprising a blood treatment device of the invention and to the blood treatment device for use as a medicament or to methods of treating an infection, preferably a blood or systemic infection, such as sepsis, and/or for the treatment of sepsis-associated acute kidney injury (AKI).

BACKGROUND OF THE INVENTION

Sepsis is one of the main causes of morbidity and mortality in critically ill patients despite the use of modern antibiotics and resuscitation therapies. Outcomes in sepsis have improved overall but mortality rates remain unacceptably high. Sepsis is the most expensive health-care problem in the USA, with a cost of more than $20 billion (Martin G S, et al 2000. N Engl J Med 2003; 348: 1546-54). Sepsis is one of the most prevalent causes of mortality in intensive care units (ICUs), and its incidence increased by more than double over the last 10 years (Kumar G, et al, Chest 2011; 140: 1223-31). According to data from the Surviving Sepsis Campaign, mortality rates from sepsis are 41% in Europe and 28.3% in the USA (Levy M M, et al Lancet Infect Dis 2012; 12: 919-24).

Acute kidney injury (AKI) or acute renal failure (ARF) is the rapid loss of the renal filtration function, which is characterized by metabolic acidosis, high potassium levels and a body fluid imbalance. AKI occurs in 55-60% of critically ill patients, and sepsis is the most common underlying cause. The overall mortality rate of AKI/ARF is about 45%, however, the mortality rate of sepsis-induced ARF is about 70% (Acute Blood Purification, Suzuki and Hirasawa; Septic Acute Renal Failure, Mori et al, Contrib Nephrol. Basel, Karger, 2010, vol 166, pp 40-46).

Blood purification therapies in septic KI typically include the elimination of pathogens, such as endotoxin or mediators that contribute to AKI, and renal replacement therapy (RRT). The adsorption of endotoxin with direct hemoperfusion using polymyxin-B immobilized fiber (PMX-DHP) makes urinary output increase while also improving renal function (Mori et al, 2010). However, currently there are no pharmacological therapies established to treat sepsis-associated acute kidney injury (SA-AKI); only supportive renal replacement therapy (RRT) is available. AKI is associated with a complex cascade of microvascular dysregulation and cellular injury that occurs via inflammation, immune dysregulation and oxidative injury. An array of novel therapies that target specific enzymes or molecules involved in these pathways are in various stages of development (Bajwa A. et al. Curr Drug Targets 2009:10:1196-1204). Despite these advances, means for treating AKI are desperately needed.

A new candidate drug in clinical development to treat or prevent sepsis associated acute kidney injury (SA-AKI) is alkaline phosphatase (AP). AP is a dephosphorylating, membrane-bound, endogenously occurring enzyme, exerting detoxifying effects through dephosphorylation of endotoxins, involved in sepsis pathogenesis and other proinflammatory compounds, including extracellular ATP. AP confers renal protection during septic AKI via the dephosphorylation of circulating lipopolysaccharide, which activates inflammatory pathways when the lipid A molecule is phosphorylated. In addition, AP converts ATP to adenosine, which exhibit protective effects on renal tubular cells. In sepsis, mitochondria release large quantities of ATP in response to cytokines and hypoxia.

Previously, clinical trials in healthy volunteers and patients with sepsis, with or without AKI, have established the tolerability and potential efficacy of purified bovine intestinal AP (Pickkers P, et al, Eur J Clin Pharmacol 2009; 65:393-402; Heemskerk S et al, Crit Care Med 2009; 37:417-23); Pickkers P et al, Crit Care 2012; 16: R14). In patients with SA-AKI, bovine intestinal AP significantly improved renal function according to the combined end point of endogenous creatinine clearance, requirement for renal replacement therapy (RRT) and duration of RRT. Following these results, a human recombinant AP has been developed as a pharmaceutically acceptable replacement for bovine-derived AP. In order to improve enzyme stability, while maintaining catalytic function, the crown domain of a human intestinal AP is replaced with the crown domain of human placental AP (Kiffer-Moreira T, et al, PLoS ONE 2014; 9: e89374).

U.S. Pat. No. 6,290,952 also discloses pharmaceutical compositions comprising AP suitable for (systemic) treatment of clinical complications induced by infections, including sepsis.

Regardless of the advances and clinical potential in administering AP in the treatment of AKI, AP exhibits a number of disadvantages in terms of its pharmacokinetics when administered to subjects as a pharmaceutical agent. AP is rapidly cleared from the blood resulting in only about 10% of the originally administered activity being present after 4 hours. As a consequence, AP has to be administered repeatedly and levels fluctuate highly, reaching suboptimal levels throughout the treatment. Considering the difficulties outlined above, there exists a significant need in the field to develop improved means for AKI treatment that provide stable physiological improvements without the difficulties evident in pharmacological treatment of this condition.

The present invention therefore relates to a blood treatment device comprising a matrix to which alkaline phosphatase (AP) is immobilized. AP has been described previously immobilized to a solid phase (EP3110977, WO2013012924, WO9955828, and Chelpanova et al, Applied Biochemistry and Microbiology, vol. 52, no. 1, p. 36-42, 2016). Immobilized AP has however not been described or suggested in the context of an extracorporeal blood treatment device suitable for treating sepsis or AKI.

SUMMARY OF THE INVENTION

In light of the prior art, the technical problem underlying the present invention is to provide alternative and/or improved means for the treatment of infections, such as sepsis, and/or renal failure associated therewith. One object of the invention is to provide improved or alternative means for infection or renal failure treatment that provide stable physiological improvements without the difficulties evident in pharmacological treatment of these conditions One objective of the invention is the provision of means for dephosphorylating extracellular adenosine triphosphate (ATP), adenosine diphosphate (ADP), adenosine monophosphate (AMP) and/or lipopolysaccharide (LPS) in the blood of a patient in need thereof.

The present invention seeks to provide such means while avoiding the disadvantages known in the prior art.

The problem is solved by the features of the independent claims. Preferred embodiments of the present invention are provided by the dependent claims.

The invention therefore relates to a blood treatment device configured to dephosphorylate extracellular adenosine triphosphate (ATP), adenosine diphosphate (ADP), adenosine monophosphate (AMP) and/or lipopolysaccharide (LPS) in the blood of a patient in need thereof in an extracorporeal blood circuit, wherein the device comprises a matrix having alkaline phosphatase (AP) immobilized thereon.

In one embodiment, the blood treatment device is located in an extracorporeal blood circuit through which the blood of the patient passes, and which comprises means for transporting blood from the patients vascular system to the blood treatment device at a defined flow rate and for returning the treated blood back to the patient.

In a further aspect, the invention therefore relates to an extracorporeal blood circuit through which the blood of a patient passes, comprising a blood treatment device as described herein and means for transporting blood from the patients vascular system to the blood treatment device at a defined flow rate and then returning the treated blood back to the patient.

The main advantage of direct incorporation of AP into a blood treatment device, such as a dialyzer or hemofilter (membrane), is increased stability of immobilized AP and the lack of clearance of AP by the body. Current kinetics of AP as a pharmacological agent involve rapid clearance and/or deactivation of AP leading to a decrease in AP activity to only about 10% of the initial administered activity after 4 hours. By immobilizing AP within an extracorporeal blood treatment device clearance of the active agent is limited or eliminated with none or only a very small loss of activity over time.

Another significant advantage of the approach described herein is the lack of need for any additional treatment or administration. By including AP into a blood treatment device suitable for extracorporeal dephosphorylation of extracellular adenosine triphosphate (ATP), adenosine diphosphate (ADP), adenosine monophosphate (AMP) and/or lipopolysaccharide (LPS) in the blood of a patient is that the therapy is automatically combined as soon as RRT or other dialysis is started. Patients suffering from renal failure are often immediately initiated on a dialysis treatment in order to compensate for failing renal function. This occurs in a significant number of sepsis cases, in which treatment speed is crucial in reducing the risk of mortality. The present invention therefore allows the incorporation of an active agent into a likely already established RRT treatment that has been initiated for the subject.

The present invention enables significant cost reductions compared to injections of AP, as the amount of AP needed when incorporated into an extracorporeal blood treatment device is far less compared to intravenous injections, due to the fast clearance of intravenously administered AP and the requirement for continuous multiple administrations.

A matrix with immobilized AP in a blood treatment device therefore leads to multiple advantages, including increasing the time during which the toxic substrate is in contact with AP, avoiding the rapid clearance of AP from the blood when administered systemically, avoiding off-target effects of AP in other organs of the body, as the AP is administered only to the blood using the extracorporeal system, avoiding the necessity of additional therapies, as AP treatment can occur concurrently with the initiation of RRT or other dialysis, thereby simultaneously dephosphorylating a toxic substrate and removing e.g. uremic toxins, excess ions and water from the blood of a patient suffering from renal failure, and a faster treatment that is particularly important in the context of sepsis, for which treatment speed is crucial in avoiding mortality.

As is shown in the examples below, AP immobilization has been achieved for multiple matrix types, including, without limitation, PES/PVP membranes, PES/PVP/Maleic Anhydride membranes, PES/PVP/chitosan membranes, epoxy-functionalized adsorber resins, amino-functionalized adsorber resin and polyacrylonitrile AN69 membranes. Unexpectedly, the AP immobilized to said matrices shows good activity, no or negligible leaching after extended flushing, and maintains excellent stability over extended time frames relevant for clinical dialysis approaches, both in buffer and human plasma. The combination of advantages using an extracorporeal approach with the unexpectedly good enzyme characteristics of immobilized AP represents a beneficial and surprisingly effective development over the prior art.

In one embodiment, the blood treatment device is a hemofilter or dialyzer.

Such an embodiment provides a combination of two functions and can be advantageously utilized as a device for dephosphorylating target proteins in the blood or blood plasma of a person in need thereof via an extracorporeal blood circuit as described herein, because the device simultaneously dephosphorylates a target protein and removes e.g. uremic toxins, excess ions and water from the blood of the patient who suffers from renal failure. Accordingly, only one device is needed for the treatment of a patient suffering from an infection or renal failure disease. The extracorporeal circuit is accordingly as such not basically different from a standard extracorporeal circuit for performing hemodialysis in the treatment of renal failure. The treatment of such patients suffering from renal failure and an infection, such as sepsis, is thus significantly simplified and may help to reduce costs for the cumulative treatment of the patients and increase the treatment options for the patients and attending physicians.

In one embodiment, the blood treatment device is a hemofilter comprising a bundle of hollow fibers and the alkaline phosphatase (AP) is immobilized to at least the lumen, and optionally the pores, of said hollow fibers of the bundle.

In one embodiment, the blood treatment device as described herein is characterized in that the matrix of the device is a hollow fiber membrane, fiber mat or flat sheet membrane, which is composed of at least one polysaccharide derivative or synthetic polymer, examples of which are provided below, to which AP is immobilized.

In some embodiments, AP is also immobilized to the pore surface(s), especially in case of larger pore membranes such as plasma separation membranes or HCO membranes.

In some embodiments, the blood treatment device can generally be designed as a hollow fiber membrane filter (hemofilter) or dialyzer, wherein the membrane constitutes the support to which AP is (at least) bound on the lumen side of the hollow fibers which is in contact with blood. The membrane can be a hemodialysis membrane for the treatment of renal failure which is additionally functionalized with said AP on its lumen side or a plasma separation membrane which is also additionally functionalized with AP on its lumen side or, alternatively on the outer side of the hollow fibers and/or its pores.

It is one object of the present invention to provide a hemofilter or hemodialyzer for the purification of blood which can be used for simultaneously treating a patient suffering from an infection, such as sepsis, or renal failure, such as SA-AKI. Due to this combined approach, the hemofilter function acts in combination and potentially synergistically with the AP treatment, leading to a RRT of which the patient is in acute need, and simultaneously treating the factors involved in infectious disease, such as LPS.

In one embodiment, the device can be a hemofilter for the treatment of renal failure and an infection, wherein the filter further comprises, in at least one of the end caps, a resin, e.g. in sponge form, or a non-woven, which is functionalized with AP for dephosphorylating the targets of interest. The targets of interest are preferably extracellular adenosine triphosphate (ATP), adenosine diphosphate (ADP) and/or lipopolysaccharide (LPS).

In one embodiment, the blood treatment device is an adsorber cartridge.

In one embodiment, the blood treatment device is located in an extracorporeal blood circuit as described herein, wherein the circuit additionally comprises a (separate) hemofilter located upstream or downstream of the adsorber cartridge.

In one embodiment, the adsorber cartridge comprises a matrix having alkaline phosphatase (AP) immobilized thereon.

In one embodiment, the blood treatment device as described herein is characterized in that the matrix comprises a support to which AP is bound, wherein the support comprises or consists of a material selected from the group consisting of hollow fiber membrane, flat sheet membrane, fiber mat, resin, non-woven and open porous foams, such as polyurethane (PU) foam.

In one embodiment, the blood treatment device as described herein is characterized in that the support is a resin, and the resin is composed of at least one polymer selected from the group consisting of alginate, chitosan, chitin, collagen, carrageenan, gelatin, cellulose, starch, pectin and sepharose; inorganic materials selected from the group consisting of zeolites, ceramics, celite, silica, glass, activated carbon and charcoal; or synthetic polymers, examples of which are provided below.

In one embodiment, the blood treatment device as described herein is characterized in that the support is a resin, and the resin is composed of at least one synthetic polymer, examples of which are provided below.

In one embodiment, the blood treatment device as described herein is characterized in that the support is a non-woven and the non-woven is composed of at least one biopolymer selected from the group consisting of polysaccharide, polylactic acid (PLA), polycaprolactone (PCL) and proteins, or of at least one inorganic material selected from the group consisting of $TiO_2$, $SiO_2$ or $Al_2O_3$, or from at least one synthetic polymer, examples of which are provided below.

In one embodiment, the blood treatment device as described herein is characterized in that the blood treatment device is an adsorption cartridge comprising a matrix, to which AP is immobilized, and is perfused with whole blood.

The device can therefore be or comprise an adsorption cartridge comprising a matrix selected from a resin or non-woven material, either of which is functionalized with AP configured for dephosphorylating the targets of interest (extracellular adenosine triphosphate (ATP), adenosine diphosphate (ADP) and/or lipopolysaccharide (LPS), also referred to as a target protein). Such a device can be a member of an extracorporeal circuit for blood treatment, configured to provide hemodialysis, hemodiafiltration, hemofiltration or plasmapheresis.

The device can be the sole blood treatment device within the blood circuit or can be located, for example, upstream or downstream of an additional hemofilter or dialyzer in a hemodialysis, hemodiafiltration or hemofiltration circuit, or can alternatively be immediately connected to the dialyzer at the blood inlet or outlet, wherein the device is configured to be perfused with whole blood. The device can also be a member of an extracorporeal plasmapheresis circuit, wherein the device is perfused with blood plasma or components thereof.

The device can also be a hybrid filter device which combines hollow fiber membranes and a matrix in the filtrate space of the filter (WO 2014/079680 A1), wherein said matrix comprises preferably of a resin which is functionalized with AP. Such a filter can be a member of an extracorporeal circuit configured for performing hemodialysis, hemodiafiltration or hemofiltration, wherein the said filter is located either upstream or downstream of the hemofilter or dialyzer for hemodialysis, hemodiafiltration or hemofiltration, or it can be used as a sole filter device within the said circuit in the absence of such dialyzer. Such device can be used with whole blood.

In one embodiment, the blood treatment device as described herein is characterized in that the extracorporeal blood circuit in which the blood treatment device is located further comprises a plasma dialyzer or centrifuge-based plasma separation system which allows for the separation of a plasma fraction from the blood, and wherein the blood treatment device is located downstream of the plasma outlet port of the plasma dialyzer. In a further aspect, the invention relates to an extracorporeal blood circuit comprising a blood treatment device as described herein, wherein the extracorporeal blood circuit comprises means for transporting blood or blood plasma from the patient's vascular system to the blood treatment device at a defined flow rate and means for returning the treated blood or blood plasma back to the patient.

The active agent of the present invention is alkaline phosphatase (AP).

AP is known in various forms, each of which is not limiting to the present invention. The device described herein is characterized by its ability to exhibit the function of AP, namely to dephosphorylate extracellular adenosine triphosphate (ATP), adenosine diphosphate (ADP), adenosine monophosphate (AMP) and/or lipopolysaccharide (LPS) in the blood of a patient in need thereof. The specific type of AP is only limited in as far as the desired function is achieved. AP has a broad specificity for phosphate esters of alcohols, amines, pyrophosphate, and phenols. It is routinely used to dephosphorylate proteins and nucleic acids and is known to dephosphorylate LPS, ATP and ADP.

Lipopolysaccharide (LPS) is a part of the outer membrane of Gram-negative bacteria and plays a major role in the inflammatory cascade observed during severe infections, such as sepsis. LPS induces both systemic and renal inflammation through signaling via its pattern recognition receptor Toll-like receptor 4 (TLR4), localized on immune cells and on proximal tubule epithelial cells (PTEC), resulting in epithelial inflammation, endothelial inflammation and hypoxia. Due to the complex pathophysiology of sepsis, which involves systemic and renal inflammation combined with renal hypoxia, to be effective a treatment should aim to target all or a combination of these processes. Alkaline phosphatase (AP), a dephosphorylating enzyme, is a molecule that exerts such a dual mechanism of action.

AP can detoxify LPS, which is composed of an oligosaccharide core component, a polysaccharide chain and the toxic lipid A part with two phosphate groups. Removal of one of these two phosphate groups by AP results in a non-toxic LPS molecule, which can still bind to TLR4 but then acts as an antagonist.

Another protective mechanism of AP is dephosphorylation of ATP, an endogenous signaling molecule released during cell stress, induced by for example inflammation and hypoxia. Excreted ATP attracts phagocytes and activates platelets and the NLRP3 inflammasome, further enhancing inflammation and tissue injury. Upon dephosphorylation by exogenous AP, ATP yields ADP, AMP and adenosine, of which the latter exerts renal protective and anti-inflammatory effects via binding to one of the four adenosine receptors A1, A2A, A2B and A3. Potentially, AP enhances the conversion of ATP into ADP, AMP and eventually adenosine, thereby increasing adenosine levels and exerting its anti-inflammatory and tissue-protective effects. The effect of AP on ADP is therefore beneficial, as the same enzyme catalyzes conversion of ATP to ADP, and further catalyzes conversion of ADP to AMP and adenosine.

As is evident from the above, the dephosphorylation of extracellular adenosine triphosphate (ATP), adenosine diphosphate (ADP), adenosine monophosphate (AMP) and/or lipopolysaccharide (LPS) in the blood of a patient in need thereof represent an effective means towards counteracting the negative effects of these pathological signaling and bacterial molecules.

In one embodiment, the alkaline phosphatase (AP) is bovine intestinal alkaline AP.

Bovine intestinal AP has been shown to be well tolerated by subjects and shows potential efficacy in various clinical settings. In patients with SA-AKI, bovine intestinal AP has significantly improved renal function according to the combined end point measurements of endogenous creatinine clearance, requirement for renal replacement therapy (RRT) and duration of RRT.

In one embodiment, the alkaline phosphatase (AP) is a recombinant and/or chimeric form of AP.

In some embodiments, a recombinant AP as described herein is employed in the invention. A preferred AP variant displays enhanced stability and good selectivity for LPS (Kiffer-Moreira T, et al, PLoS ONE 2014; 9: e89374).

Earlier studies on the structure of placental AP (PLAP) revealed an active site, with two active Zn2+ residues (Zn1 and Zn2) and a third metal ion site, occupied by Mg2+. While Zn2 is buried within the molecule, Zn1 is easily accessible and its reactivity can be modulated. Both Zn1 and Zn2 coordinate with highly conserved amino acids and mutagenesis studies uncovered a major role for residue E429 in determining the affinity of Zn1, and thus the stability and catalytic properties of the PLAP active site as well as determining the overall thermal properties of the enzyme. Introducing the well-characterized crown domain of PLAP, harboring the critical E429 residue, into the intestinal human AP structure improves enzyme stability while preserving or enhancing catalytic function of the resulting chimeric enzyme. The recombinant AP produced displays greatly increased heat stability, increased Zn2+ binding affinity, increased transphosphorylation, a higher turnover number and narrower substrate specificity, with comparable selectivity for bacterial LPS, than the parent human intestinal AP isozyme (Kiffer-Moreira T, et al, PLoS ONE 2014; 9: e89374).

The matrix material on the device of the present invention can be essentially any material suitable for bringing into contact with human blood and to which AP can be immobilized.

In one embodiment, the matrix, preferably the hollow fiber membrane, to which the alkaline phosphatase (AP) is immobilized, comprises or consists of a polysulfone, poly(ether)sulfone (PES) and/or polyaryl(ether)sulfone (PAES), and polyvinylpyrrolidone (PVP).

In one embodiment, the matrix, preferably the hollow fiber membrane, to which the alkaline phosphatase (AP) is immobilized, comprises or consists of a polysulfone, PES and/or PAES, and PVP, with an additive selected from chitosan and/or maleic anhydride-alt-1-octadecene.

Accordingly, the device is a hollow fiber membrane dialyzer which is designed for use in hemodialysis and wherein the lumen side of the hollow fibers of the hemodialyzer are functionalized with alkaline phosphatase (AP).

According to one aspect of the invention, said hemodialyzers are based on membranes prepared from polymers and polymeric blends. The membrane materials (with the exception of EVAL®) are primarily hydrophobic and, therefore, are combined with hydrophilic additives (such as polyvinylpyrrolidone (PVP) or PEG) or are processed with hydrophilic copolymers such as methallyl sulfonate.

Examples for commercially available materials and dialyzers which can be used according to the invention comprise those listed, for example, in the Table below. Membranes prepared from hydrophobic/hydrophilic polymer blends are the predominant type of synthetic polymeric membrane. Their hydrophobic-based material is either polysulfone or polyethersulfone (polyarylethersulfone), and they further comprise a hydrophilic component, which often is PVP. Polyethersulfone- and polysulfone-based membranes contain small amounts of water and are, in contrast to other membranes, free from pore stabilizers. These membranes are especially suitable according to the present invention, as are polyacrylonitrile containing membranes.

TABLE

Hemofilter membrane materials and manufacturers

| Synthetic polymers | Membrane | Manufacturer |
| --- | --- | --- |
| Polyethersulione/polyvinylpyrrolidone/polyamide | Polyamix ™ | Gambro |
| Polyethersulfonepolyvinylpyrrolidone | Revaclear DIAPES ®, PUREMA ® | Gambro Membrana |

TABLE-continued

Hemofilter membrane materials and manufacturers

| Synthetic polymers | Membrane | Manufacturer |
|---|---|---|
| | POLYNEPHRONTM | Nipro |
| | ARYLANE ® | Hospal |
| | Polyphen ® | Minntech |
| Polysulfone/polyvinypyrrolidone | Polysulfone ®, Helixone ® | Fresenius Medical Care |
| | Toraysulfone ® | Toray Industries |
| | Diacap ®alpha | B. Braun |
| | Minntech PS | Minntech |
| | REXBRANE, APS, VitabranE, Biomembranel PEG | Asahi Kasei Kuraray Medical Co. Ltd. |
| Polyacrylonitrile | AN69 ®ST, Evodial, oXiris, | Hospal |
| Polymethylmethacrylate | PMMA ® | Toray Industries |
| Ethylenvinylalcohol copolymer | EVAL ® | Asahi Kuraray Membrane Manufacturing Co., Ltd. |
| Polyester/polyvinypyrrolidone | PEPA ® | Nikklso |

According to one aspect of the invention, polysulfone/PVP membranes are used. All polysulfone-based dialysis membranes possess a foam-like support structure that is designed to achieve specific separation characteristics. The increased hydraulic resistance of a foam-like support structure is partially compensated for by a reduction in wall thickness. Examples for this type of membranes, are, for example, those mentioned in the above table, for example, Helixone membranes from Fresenius Medical Care.

According to another aspect of the present invention, polyethersulfone/PVP/polyamide membranes are used. The so-called Polyamix membrane has a unique asymmetric, three-layer structure in which the outer layer, referred to as the supporting layer, is characterized by a very open finger-like morphology. The actual inner separation layer of the membrane consists of an extremely thin inner skin supported by an intermediate layer. This middle layer forms a foam-like structure that is very permeable. Thus, low resistance for convection and diffusion is ensured. The outer layer provides high mechanical stability.

According to yet another aspect of the present invention, polyethersulfone/PVP or poly(aryl)ethersulfone membranes are used. Most membranes made of polyethersulfone and polyvinylpyrrolidone are characterized by their asymmetric structure, a dense selective inner skin, which is in contact with blood, and a supportive porous outer layer. By appropriately adjusting the membrane-manufacturing parameters, as well as using PVP of different molecular weights, the underlying membranes physicochemical properties, morphological structure, solute-rejection behavior, and filtration performance are refinable.

The manufacture of polysulfone/PVP based membranes, including those prepared from PES or PAES, is comparable to the production of other hollow fiber membranes and is basically known in the art (see, for example, Boschetti-de-Fierro et al., Membrane Innovation in Dialysis, Ronco (ed): Expanded Hemodialysis—Innovative Clinical Approach in Dialysis. Contrib Nephrol. Basel, Karger, 2017, vol 191, pp 100-114). For optimized applications, the inner diameter of a hollow fiber membrane ranges from 170 to 220 μm. Synthetic polymeric membranes have a wall thickness of between 25 and 55 μm. The effective membrane surface area of the dialyzer chosen to treat a patient must be adjusted to the size of the patient. Pediatric filters (for small patients) have a surface area between 0.01 and 0.6 m2, and standard filters for adults range from 1.0 $m^2$ to 2.4 $m^2$.

In one embodiment, the matrix, preferably the hollow fiber membrane, to which the alkaline phosphatase (AP) is immobilized, comprises or consists of a copolymer of acrylonitrile and sodium methallyl sulfonate.

The blood purification device therefore preferably comprises polyacrylonitrile (PAN) membranes comprising i) a copolymer of acrylonitrile and sodium methallyl sulfonate, ii) a polyethyleneimine, and iii) heparin on which AP has been immobilized. Polyacrylonitrile was the first synthetic material developed for dialysis membranes. The material of the old AN69 membrane developed by Hospal is a copolymer of acrylonitrile and sodium methallyl sulfonate. This combination is crucial and includes the addition of sodium methallyl sulfonate, which influences membrane structure. WO 2007/148147 A1 describes the use, on a membrane preferably based on a copolymer of acrylonitrile and sodium methallyl sulfonate, of a solution of a polymer carrying anionic or anionizable groups in the colloidal form and in an acidic medium, in particular by mixing, for example, a solution of polymer carrying anionic or anionizable groups with a solution of organic polyacid in a specific proportion with respect to said polymer, which results in an increase in both the quantity of polymer grafted to the surface of the membrane and the availability of free cationic or cationizable groups at the surface of this membrane coating. The membrane described allows a large quantity of compounds carrying anionic or anionizable groups to be bound.

In one embodiment, the matrix, preferably the hollow fiber membrane, to which the alkaline phosphatase (AP) is immobilized, comprises or consists of polymethylmethacrylate.

According to this embodiment, polymethylmethacrylate hollow fiber membranes are preferably employed. This high-flux membrane is prepared from modified polymethylmethacrylate (PMMA). PMMA based hemofilters are commercially available and have been used in the treatment of sepsis induced AKI. Known hemofilters comprising a PMMA membrane are, for example, Filtryzer® NF (NF) and conventional Filtryzer® BG (BG) provided by Toray (Sakai, in: High Performance Membrane Dialyzers. Saito et al., eds. Contributions to Nephrology, Vol 173. Basel: Karger; 2011: 137-147).

According to the invention, AP is immobilized on a matrix of the device of the present invention. Essentially any means for immobilizing to the matrix are envisaged in the present invention. In some embodiments, the AP is immobilised to the matrix such that it remains stably attached during perfusion with blood in the context of an extracorporeal blood circuit, as would be employed in the treatment of renal failure. Any form of immobilisation that provides a stable attachment between AP and the matrix is suitable, preferably forms of immobilisation leading to no or negligible loss of AP from the matrix during employment of the device as described herein in a blood circuit.

In further embodiments of the invention, both covalent (such as cross-linking) and noncovalent (such as ionic interactions) forms of attachment are envisaged.

In further inventive, capable of the population and chemistry in which. These means of immobilisation depending on the particular matrix material employed in the device and the particular location of the device in an extracorporeal blood treatment circuit.

In one embodiment, the alkaline phosphatase (AP) is immobilized to the matrix, preferably using 1-Ethyl-3-(3-dimethylaminopropyl) carbodiimide (EDC) treatment, via an ester linkage resulting from a reaction between an OH group of a polysulfone, poly(ether)sulfone (PES) and/or polyaryl(ether)sulfone (PAES) and a COOH group of AP.

In one embodiment, the alkaline phosphatase (AP) is immobilized to the matrix, preferably using 1-Ethyl-3-(3-dimethylaminopropyl) carbodiimide (EDC) treatment, via a peptide linkage resulting from a reaction between an $NH_2$ group of chitosan and a COOH group of AP.

In one embodiment, the alkaline phosphatase (AP) is immobilized to the matrix, preferably using 1-Ethyl-3-(3-dimethylaminopropyl) carbodiimide (EDC) treatment, via a peptide linkage resulting from a reaction between a COOH group created by maleic anhydride-alt-1-octadecene and an $NH_2$ group of AP.

1-Ethyl-3-(3-dimethylaminopropyl) carbodiimide (EDC) is a reagent known in the art as useful for producing crosslinks between OH and COOH groups, or between $NH_2$ and COOH groups. Because proteins are rich in $NH_2$ and COOH groups, EDC chemistry represents an effective means of immobilizing AP to a matrix. A skilled person will adjust immobilisation conditions and methods according to the particular matrix (membrane) material employed in the device.

Carboxylic acids (—COOH) exist at the C-terminus of each polypeptide chain and in the side chains of aspartic acid (Asp, D) and glutamic acid (Glu, E). Like primary amines, carboxyls are usually on the surface of protein structure. Carboxylic acids are reactive towards carboiimides, such as EDC.

EDC and other carbodiimides are zero-length cross-linkers. They typically cause direct conjugation of carboxylates (—COOH) to primary amines (—NH2) without becoming part of the final amide-bond crosslink between target molecules. Because peptides and proteins contain multiple carboxyls and amines, direct EDC-mediated cross-linking can cause random polymerization of polypeptides. Nevertheless, this reaction chemistry is used widely in immobilization procedures.

EDC reacts with carboxylic acid groups to form an active O-acylisourea intermediate that is easily displaced by nucleophilic attack from primary amino groups in the reaction mixture. The primary amine forms an amide bond with the original carboxyl group, and an EDC by-product is released as a soluble urea derivative. The O-acylisourea intermediate is unstable in aqueous solutions. Failure to react with an amine results in hydrolysis of the intermediate, regeneration of the carboxyls, and the release of an N-unsubstituted urea. EDC crosslinking is efficient in acidic (pH 4.5) conditions and is typically employed in buffers devoid of extraneous carboxyls and amines. MES buffer (4-morpholinoethanesulfonic acid) is a suitable carbodiimide reaction buffer. Phosphate buffers and neutral pH (up to 7.2) conditions are compatible with the reaction chemistry, but with lower efficiency. Increasing the amount of EDC in a reaction solution can compensate for the reduced efficiency.

In some embodiments, immobilization relates to cross-linking OH groups from a matrix material or surface to a COOH group of AP. In further embodiments, such immobilization relates to crosslinking an $NH_2$ group of chitosan and a COOH group of AP. In further embodiments, such immobilization relates to crosslinking a COOH group created by maleic anhydride-alt-1-octadecene and an $NH_2$ group of AP.

Alternative means of crosslinking AP to the matrix of the device are available to a skilled person and can be employed without undue effort. Depending on the matrix, suitable chemistries can be employed. Some matrix-materials can be activated for direct coupling to AP. Other supports are made with nucleophiles or other functional groups that can be linked to proteins using crosslinkers. Carbodiimides such as DCC and EDC are very useful for coupling proteins to carboxy- and amine-activated glass, plastic and polysaccharide supports. Carbodiimide procedures are usually one-step methods; however, two-step methods are possible if reactions are performed in organic solvents, or if NHS or Sulfo-NHS chemistry is used to enhance the reaction. In some embodiments, spacers may be used. Useful spacers are diaminodipropylamine (DADPA), ethylenediamine, hexanediamine, 6-amino-caproic acid and any of several amino acids or peptides. Spacer arms help to overcome steric effects when the AP is immobilized too near the matrix to allow access of AP to its targets.

A further aspect of the invention relates to a method for manufacturing a blood treatment device as described herein, wherein said device is configured to dephosphorylate extracellular adenosine triphosphate (ATP), adenosine diphosphate (ADP), adenosine monophosphate (AMP) and/or lipopolysaccharide (LPS) in the blood of a patient in need thereof, comprising immobilizing alkaline phosphatase (AP) to a matrix.

In one embodiment of the method, the blood treatment device is a hemofilter comprising a bundle of hollow fiber membranes and the alkaline phosphatase (AP) is immobilized to at least the lumen, and optionally the pores, of said hollow fibers of the bundle.

In one embodiment of the method, the alkaline phosphatase (AP) is covalently bound to the matrix, the method comprising treatment of said matrix and/or AP using a carbodiimide compound, preferably 1-Ethyl-3-(3-dimethylaminopropyl) carbodiimide (EDC). Suitable methods employing specific EDC chemistries and protocols are disclosed in more detail below in the examples.

The method of the invention is highly advantageous, as producing the device does not require any fundamental change to the structure, function or usability of a standard blood treatment device, such as an adsorber or hemofilter. Existing blood treatment adsorbers or hemofilters can also be treated subsequently (after manufacture) with AP in order to immobilize the active agent and prepare the device for use. Since the dialyzer does not structurally change, but is only modified once manufactured, the need for investment in additional manufacturing is limited.

In some embodiments, the device for extracorporeal therapy as produced using the method described herein, containing immobilized AP, may preferably be filled with or stored in a buffer or other solution wherein the matrix comprising the immobilized AP is immersed in said buffer or solution, with the presence of $Mg^{2+}$ in a concentration of 0.1 to 2, preferably 0.1 to 1 mmol/L, and a $Zn^{2+}$ in a concentration of 5 to 150, preferably 10 to 100 μmol/L. Some variation in said values is possible, depending on the AP employed, whilst maintaining the desired AP activity.

In some embodiments, the method of manufacturing a blood treatment device as described herein comprises a PEI coating process of a membrane, preferably a polyacrylonitrile membrane, more preferably an AN69 membrane or hollow fiber bundle, preferably using an acidic solution, more preferably a citric acid solution, followed by glutaraldehyde treatment and AP immobilization.

As demonstrated in the examples below, a particularly effective PEI coating process in terms of subsequent GA/AP functionalization and AP activity has been developed. In a preferred embodiment, polyacrylonitrile membrane, preferably an AN69 membrane or hollow fiber bundle, is treated using PEI in an acidic solution (preferably PEI at 100-300, or about 200 mg/kg, in a citric acid solution, preferably at 10-300, preferably 200 mg/g).

In one embodiment, an optimal PEI density of 0.5 to 5, preferably 1 to 3 μmol/g of hollow fiber membrane is employed (prior to GA and AP treatment).

In one embodiment, the method of manufacturing a blood treatment device as described herein comprises GA treatment of a PEI-treated membrane, wherein said GA is applied to the membrane at an alkaline pH, preferably between 7.1-11 pH, more preferably between 7.3-10.5 pH, more preferably around 7.4 or 9.9 pH. These pH values lead to effective GA treatment and subsequently an unexpectedly stable and active immobilized AP.

In one embodiment, the method of manufacturing a blood treatment device as described herein comprises AP treatment of a PEI- and GA-treated membrane, wherein said AP is applied to the membrane in solution at an alkaline pH, preferably between 7.1-11 pH, more preferably between 7.3-10.5 pH, more preferably around 7.4 or 9.9 pH. These pH values lead to an unexpectedly stable and active immobilized AP.

In a preferred embodiment, PEI-treatment is conducted, preferably using a polyacrylonitrile membrane, more preferably an AN69 membrane or hollow fiber bundle, at a pH of between 7.1-7.8, more preferably at about 7.4, followed by AP treatment in solution at a pH of 8.5-10.5, more preferably around 9.9.

In some embodiments, the matrix with immobilized AP is subsequently sterilized. Surprisingly, the sterilization of matrices tested below does not lead to significant reduction in AP activity, that would be problematic for clinical application. In one embodiment, gamma sterilization is employed. In one embodiment, EtO gas sterilization is employed. In one embodiment, heat sterilization (steam sterilization) is not employed.

In a further aspect, the invention relates to the blood treatment device as described herein for use as a medicament in the treatment of an infection, preferably a blood or systemic infection.

In a further aspect, the invention relates to the blood treatment device as described herein for use as a medicament in the treatment of any disease associated with pathological levels of extracellular adenosine triphosphate (ATP), adenosine diphosphate (ADP) and/or lipopolysaccharide (LPS). LPS is commonly known as a pathologic molecule associated with multiple infectious diseases. The dephosphorylation of LPS and detoxification of the molecule employing the present invention enables effective counteraction of the pathological effects of LPS.

In one embodiment, the invention relates to the blood treatment device as described herein for use as a medicament in the treatment of sepsis or septic shock.

In one embodiment, the invention relates to the blood treatment device as described herein for use as a medicament in the treatment of infection-associated renal disfunction. In one embodiment, the infection-associated renal disfunction is sepsis-associated acute kidney injury (AKI, or SA-AKI).

In one embodiment, the treatment comprises continuous renal replacement therapy in an acute setting, preferably in an intensive care unit (ICU).

According to one aspect, the present invention provides a method of treating or ameliorating at least one symptom of such a disorder.

It is therefore a further object of the present invention to provide a method of treating or ameliorating at least one symptom of a disorder associated with in pathological levels of extracellular adenosine triphosphate (ATP), adenosine diphosphate (ADP), adenosine monophosphate (AMP) and/or lipopolysaccharide (LPS) in a patient, wherein the method comprises the step of extracorporeally dephosphorylating extracellular adenosine triphosphate (ATP), adenosine diphosphate (ADP), adenosine monophosphate (AMP) and/or lipopolysaccharide (LPS) in the blood from the patient by passing the blood or the blood plasma of the patient over a matrix which is configured as described herein and then returning the treated blood back to the patient.

It is therefore one object of the present invention to provide for devices, extracorporeal circuits and methods of treating or preventing infection, preferably a blood or systemic infection, sepsis or septic shock, infection-associated renal disfunction or a sepsis-associated acute kidney injury (AKI) wherein the devices are placed in an extracorporeal blood treatment circuit and are configured to dephosphorylate extracellular adenosine triphosphate (ATP), adenosine diphosphate (ADP) and/or lipopolysaccharide (LPS).

DETAILED DESCRIPTION OF THE INVENTION

All cited documents of the patent and non-patent literature are hereby incorporated by reference in their entirety. All terms are to be given their ordinary technical meaning, unless otherwise described herein.

The present invention is based on dephosphorylating extracellular adenosine triphosphate (ATP), adenosine diphosphate (ADP), adenosine monophosphate (AMP) and/or lipopolysaccharide (LPS) in the blood of a patient extracorporeally, using AP immobilized to a matrix within a blood treatment device, such as a hemofilter or an adsorber cartridge to which alkaline phosphatase (AP) is immobilized, and then returning the treated blood back to the patient.

Extracorporeal Circuits and Treatments:

Extracorporeal systems, into which the novel blood treatment device of the present invention can be integrated, are known in the prior art. An extracorporeal procedure or system is a medical procedure or system which is performed or positioned outside the body. This relates to a common procedure in which blood is taken from a patients circulation to have any given process applied to it before it is returned to the circulation. The apparatus carrying the blood outside the body is termed the extracorporeal blood circuit. Suitable apparatus components, such as tubing, connectors, pumps and the like, are available to a skilled person.

According to the invention, the expression "extracorporeal blood purification" refers preferably to the process of removing substances from body fluids through their clearance from flowing blood in a diverted circuit outside the patient's body (extracorporeal). Said substances may include endogenous toxins (i.e., uremic toxins), exogenous poisons (i.e., ethylene glycol or fungal toxin), administered drugs, viruses, bacteria, antibodies and proteins (i.e., IMHA, myasthenia gravis), abnormal cells (i.e., leukemia), and excessive water. Therapeutic procedures include hemodialysis, including intermittent hemodialysis (HD, HDF, HF) and continuous renal replacement therapy (CRRT); hemoperfusion; and therapeutic apheresis.

The expression "blood" as used herein refers to whole blood which contains all components of the blood of an organism, including red cells, white cells, and platelets suspended in plasma. The expression "blood plasma" refers to the fluid, composed of about 92% water, 7% proteins such as albumin, gamma globulin, fibrinogen, complement factors, clotting factors, and 1% mineral salts, sugars, fats, electrolytes, hormones and vitamins which forms part of whole blood but no longer contains red and white cells and platelets. In the context of the present invention, the expression "blood plasma" also refers to specific fractions of the above defined blood plasma in its standard meaning, such as, for example, blood serum.

According to one aspect, blood flow rates in an extracorporeal blood purification circuit are between 20 ml and 700 ml/min. Typical dialysate flow rates in an extracorporeal circuit comprising a hemodialyzer for the treatment of renal failure either in addition to the blood treatment device according to the invention or in cases where the hemodialyzer in addition is configured to immobilize a target protein is in the range of between 0.5 l/h and 800 ml/min.

In hemodialysis, blood is circulated in an extracorporeal circuit and its composition is modified by the mass transfer of solute and water by diffusive and/or convective forces across an interfacing semipermeable membrane. The magnitude and spectrum of the solute transfer is predicated on the nature of the force(s) imposed across the membrane, on the chemical and physical characteristics of the solute, especially also including size, and the structural properties of the membrane. Hemodialysis is a standard treatment for patients suffering from renal failure.

Hemoperfusion is an adsorptive extracorporeal therapy used to manage endogenous and exogenous intoxications that cannot be cleared efficiently by hemodialysis. Adsorption is the principle of molecular attachment of a solute, such as protein, to a material surface (a matrix). In contrast to the physical separation between blood and dialysate that occurs during hemodialysis, during hemoperfusion blood is exposed directly to an adsorbent with the capacity to selectively or non-selectively bind solutes within the blood path.

In therapeutic apheresis blood is separated into its component fractions, for example by centrifugation or by means of a plasma membrane or filter, and the fraction containing the solute which shall be removed, generally the plasma fraction, is specifically treated prior to return to the patient. The present invention provides for an apheresis treatment in which plasma (containing the target proteins) is removed from the patient's flowing blood and, after having been contacted with a device or matrix according to the invention is returned to the patient (FIG. 5). Typical plasma flow rates in an extracorporeal circuit wherein the blood treatment device is perfused with blood plasma is in the range of between 7 ml/min and 250 ml/min.

According to one aspect, the extracorporeal blood circuit according to the invention is configured to perform hemodialysis. In this case, the device according to the invention is, for example, a hemodialyzer which additionally has been configured to immobilize a target protein according to the invention. The circuit can be operated in different treatment modes depending on the medical need, including hemodialysis, hemodiafiltration, hemofiltration mode.

According to one aspect, the device is configured to perform "Renal replacement therapy" (RRT), which relates to a therapy that is employed to replace the normal blood-filtering function of the kidneys. The hemodialysis, hemofiltration, and hemodiafiltration may be continuous or intermittent and can use an arteriovenous route (in which blood leaves from an artery and returns via a vein) or a venovenous route (in which blood leaves from a vein and returns via a vein). This results in various types of RRT.

For example, the renal replacement therapy may be selected from the group of, but not limited to continuous renal replacement therapy (CRRT), continuous hemodialysis (CHD), continuous arteriovenous hemodialysis (CAVHD), continuous venovenous hemodialysis (CVVHD), continuous hemofiltration (CHF), continuous arteriovenous hemofiltration (CAVH or CAVHF), continuous venovenous hemofiltration (CVVH or CVVHF), continuous hemodiafiltration (CHDF), continuous arteriovenous hemodiafiltration (CAVHDF), continuous venovenous hemodiafiltration (CVVHDF), intermittent renal replacement therapy (IRRT), intermittent hemodialysis (IHD), intermittent venovenous hemodialysis (IVVHD), intermittent hemofiltration (IHF), intermittent venovenous hemofiltration (IVVH or IVVHF), intermittent hemodiafiltration (IHDF) and intermittent venovenous hemodiafiltration (IVVHDF).

According to a preferred embodiment, the extracorporeal blood circuit according to the invention is configured to provide continuous renal replacement therapy (CCRT). Continuous renal replacement therapies (CRRT) are slow dialysis treatments that are provided as a continuous 24 hour per day therapy, mostly to critically ill patient in an ICU setting. Like in intermittent HD for chronic renal failure patients, solute removal with CRRT is achieved either by convection (hemofiltration), diffusion (hemodialysis), or a combination of both these methods (hemodiafiltration). This process requires the use of replacement fluid to prevent iatrogenic acidosis and electrolyte depletion as well as excessive fluid removal. CRRT and how to use it is known in the art.

According to another aspect, the extracorporeal blood circuit according to the invention is configured to perform hemoperfusion. Accordingly, the blood treatment device according to the invention is perfused with whole blood and is located within an extracorporeal circuit (FIG. 3). According to one aspect of the invention, the device is a cartridge comprising a membrane, non-woven or resin to which AP has been bound. According to one aspect, when the cartridge's matrix comprises a bundle of hollow fiber membrane to which AP is bound, the treatment mode can be hemoperfusion with closed dialysate/filtrate ports. According to yet another aspect, the cartridge can be located downstream or upstream of a hemodialyzer which is configured to perform hemodialysis on the blood of a patient (FIGS. 4A and 4B) and can be operated in different treatment modes selected from hemodialysis, hemodiafiltration and hemofiltration.

According to one aspect, the blood treatment device is a filter comprising both hollow fibers and a resin in the filtrate space of the filter as described above. The filter can be operated in hemoperfusion mode or, if combined with a hemodialyzer which can be located upstream or downstream of the device according to the invention, the treatment mode can be hemodialysis, hemodiafiltration or hemofiltration. According to yet another embodiment of the invention, the devices according to the invention may be regenerated in between treatments.

According to one aspect, the hollow fiber membrane of said device is a plasma separation membrane which allows passage of the blood plasma together with the targets contained therein to pass the membrane and interact with the matrix in the filtrate space, thereby allowing the targets to be dephosphorylated by AP. The cleansed plasma will reenter the hollow fiber membranes within the same device and the blood can return to the patient. Such a device can be located in the extracorporeal circuit either upstream or downstream of a hemodialyzer, such as described in WO 2014/079681 A2, or it can be used as a sole hemoperfusion device within the circuit. In another aspect, the AP can also or exclusively be bound to the plasma separation membrane as described above, for example to the outside and/or pores of the membrane. The resin in the filtrate space can, in one aspect, be configured to remove the same or a different target protein.

Typically, devices according to the invention are designed as cylinders with a cylindrical housing having at least one inlet and at least one outlet for the blood or blood plasma which is treated with it. Where the device is a hemodialyzer which in addition to the removal of at least one target protein serves for the treatment of renal failure in HD, HDF or HF, the device further comprises an inlet and an outlet for dialysis fluid. Device configurations which can be used according to the invention are generally known and are within the scope of this invention.

According to another embodiment, the extracorporeal blood circuit comprises a hemocompatible adsorber for the separation of protein-bound uremic toxins contained in the blood or blood plasma of a patient, as described in US 2018/0369783. The hemocompatible adsorber is suitable for separation of protein-bound uremic toxins having a molecular mass of <500 g/mol regarding their carrier proteins in order to make the uremic toxins dialyzable with hemodialysis, wherein the hemocompatible material comprises a polymer based on a cyclic oligosaccharide or a derivative thereof disposed on a solid carrier component in at least one layer. This kind of hemocompatible adsorber is thus suited for the selective and effective removal of albumin-bound toxins with hydrophobic and/or charged domains up to a molecular mass of about 500 Da (e.g. indoxyl sulfate, p-cresol, hippuric acid, or phenylacetic acid) to support ordinary extracorporeal blood treatment (e. g. hemodialysis or liver dialysis).

Alkaline Phosphatase:

As used herein, "alkaline phosphatase" (also known as AP, ALP, ALKP, ALPase, Alk Phos) or basic phosphatase is a homodimeric protein enzyme of about 86 kilodaltons, as described in more detail herein. Each monomer typically contains five cysteine residues, two zinc atoms, and one magnesium atom important to its catalytic function, and it is optimally active at alkaline pH environments. AP has the physiological role of dephosphorylating compounds. The enzyme is found across a multitude of organisms, prokaryotes and eukaryotes alike, with the same general function but in different structural forms suitable to the environment they function in. The enzyme is typically heat stable and not sensitive to the immobilization reaction chemistries disclosed herein.

A preferred embodiment of AP relates to bovine intestinal alkaline phosphatase, which is commercially available (e.g. from Sigma-Aldrich; P0114) and can be immobilized to a device matrix using both established techniques and the techniques described herein.

Bovine intestinal alkaline phosphatase is a dimeric, membrane-derived glycoprotein. At least three isoforms exist, which typically possess two N-linked and one or more 0-linked glycans per monomer. A commercially available product is available in solution in 50% glycerol containing e.g. 5 mM Tris, 5 mM MgCl2 and 0.1 mM ZnCl2, at pH 7.0. One DEA unit biAP from Sigma-Aldrich will typically hydrolyze 1 μmole of 4-nitrophenyl phosphate per minute at pH 9.8 at 37° C.

One exemplary protein sequence of intestinal alkaline phosphatase (Bos Taurus) is according to GenBank: AAA30571.1, shown below in SEQ ID NO 1. Isozymes of bovine intestinal alkaline phosphatase, as described in Besman and Coleman (J Biol Chem. 1985 Sep. 15; 260(20): 11190-3) are also envisaged for the present invention.

```
SEQ ID NO 1:
MQGACVLLLLGLHLQLSLGLVPVEEEDPAFWNRQAAQALDVAKKLQPIQT

AAKNVILFLGDGMGVPTVTATRILKGQMNGKLGPETPLAMDQFPYVALSK

TYNVDRQVPDSAGTATAYLCGVKGNYRTIGVSAAARYNQCKTTRGNEVTS

VMNRAKKAGKSVGVVTTTRVQHASPAGAYAHTVNRNWYSDADLPADAQMN

GCQDIAAQLVNNMDIDVILGGGRKYMFPVGTPDPEYPDDASVNGVRKRKQ

NLVQAWQAKHQGAQYVWNRTALLQAADDSSVTHLMGLFEPADMKYNVQQD

HTKDPTLQEMTEVALRVVSRNPRGFYLFVEGGRIDHGHHDDKAYMALTEA

GMFDNAIAKANELTSELDTLILVTADHSHVFSFGGYTLRGTSIFGLAPSK

ALDSKSYTSILYGNGPGYALGGGSRPDVNDSTSEDPSYQQQAAVPQASET

HGGEDVAVFARGPQAHLVHGVEEETFVAHIMAFAGCVEPYTDCNLPAPTT

ATSIPDAAHLAASPPPLALLAGAMLLLLAPTLY
```

One exemplary sequence of alkaline phosphatase is the human precursor protein according to GenBank: AAA51700.1, as shown below in SEQ ID NO 2.

```
SEQ ID NO 2:
MQGPWVLLLLGLRLQLSLGIIPVEEENPDFWNRQAAEALGAAKKLQPAQT

AAKNLIIFLGDGMGVSTVTAARILKGQKKDKLGPETFLAMDRFPYVALSK

TYSVDKHVPDSGATATAYLCGVKGNFQTIGLSAAARFNQCNTTRGNEVIS

VMNRAKKAGKSVGVVTTTRVQHASPAGTYAHTVNRNWYSDADVPASARQE

GCQDIATQLISNMDIDVILGGGRKYMFPMGTPDPEYPDDYSQGGTRLDGK

NLVQEWLAKHQGARYVWNRTELLQASLDPSVTHLMGLFEPGDMKYEIHRD

STLDPSLMEMTEAALLLLSRNPRGFFLFVEGGRIDHGHHESRAYRALTET

IMFDDAIERAGQLTSEEDTLSLVTADHSHLFSFGGYPLRGSSIFGLAPGK

ARDRKAYTVLLYGNGPGYVLKDGARPDVTESESGSPEYRQQSAVPLDGET

HAGEDVAVFARGPQAHLVHGVQEQTFIAHVMAFAACLEPYTACDLAPRAG

TTDAAHPGPSVVPALLPLLAGTLLLLGTATAP
```

One exemplary sequence of alkaline phosphatase is the human protein according to GenBank: AAB59378.1, as shown below in SEQ ID NO 3. Alternative exemplary human AP sequences are also known under GenBank Accession numbers AAC97139.1, AAA98616.1, CAA39425.1, AAA98617.1.

SEQ ID NO 3:
MISPFLVLAIGTCLTNSLVPEKEKDPKYWRDQAQETLKYALELQKLNTNV

AKNVIMFLGDGMGVSTVTAARILKGQLHHNPGEETRLEMDKFPFVALSKT

YNTNAQVPDSAGTATAYLCGVKANEGTVGVSAATERSRCNTTQGNEVTSI

LRWAKDAGKSVGIVTTTRVNHATPSAAYAHSADRDWYSDNEMPPEALSQG

CKDIAYQLMHNIRDIDVIMGGGRKYMYPKNKTDVEYESDEKARGTRLDGL

DLVDTWKSFKPRYKHSHFIWNRTELLTLDPHNVDYLLGLFEPGDMQYELN

RNNVTDPSLSEMVVVAIQILRKNPKGFFLLVEGGRIDHGHHEGKAKQALH

EAVEMDRAIGQAGSLTSSEDTLTVVTADHSHVFTFGGYTPRGNSIFGLAP

MLSDTDKKPFTAILYGNGPGYKVVGGERENVSMVDYAHNNYQAQSAVPLR

HETHGGEDVAVFSKGPMAHLLHGVHEQNYVPHVMAYAACIGANLGHCAPA

SSAGSLAAGPLLLALALYPLSVLF

Also encompassed as an exemplary embodiment is human intestinal-type alkaline phosphatase precursor according to GenBank Reference Sequence NP_001622.2, as in SEQ ID NO 4.

SEQ ID NO 4:
MQGPWVLLLLGLRLQLSLGVIPAEEENPAFWNRQAAEALDAAKKLQPIQK

VAKNLILFLGDGLGVPTVTATRILKGQKNGKLGPETPLAMDRFPYLALSK

TYNVDRQVPDSAATATAYLCGVKANFQTIGLSAAARFNQCNTTRGNEVIS

VMNRAKQAGKSVGVVTTTRVQHASPAGTYAHTVNRNWYSDADMPASARQE

GCQDIATQLISNMDIDVILGGGRKYMFPMGTPDPEYPADASQNGIRLDGK

NLVQEWLAKHQGAWYVWNRTELMQASLDQSVTHLMGLFEPGDTKYEIHRD

PTLDPSLMEMTEAALRLLSRNPRGFYLFVEGGRIDHGHHEGVAYQALTEA

VMFDDAIERAGQLTSEEDTLTLVTADHSHVFSFGGYTLRGSSIFGLAPSK

AQDSKAYTSILYGNGPGYVFNSGVRPDVNESESGSPDYQQQAAVPLSSET

HGGEDVAVFARGPQAHLVHGVQEQSFVAHVMAFAACLEPYTACDLAPPAC

TTDAAHPVAASLPLLAGTLLLLGASAAP

A shorter version, as in SEQ ID 5, is also envisaged:

SEQ ID NO 5:
VIPAEEENPAFWNRQAAEALDAAKKLQPIQKVAKNLILFLGDGLGVPTVT

ATRILKGQKNGKLGPETPLAMDRFPYLALSKTYNVDRQVPDSAATATAYL

CGVKANFQTIGLSAAARFNQCNTTRGNEVISVMNRAKQAGKSVGVVTTTR

VQHASPAGTYAHTVNRNWYSDADMPASARQEGCQDIATQLISNMDIDVIL

GGGRKYMFPMGTPDPEYPADASQNGIRLDGKNLVQEWLAKHQGAWYVWNR

TELMQASLDQSVTHLMGLFEPGDTKYEIHRDPTLDPSLMEMTEAALRLLS

RNPRGFYLFVEGGRIDHGHHEGVAYQALTEAVMFDDAIERAGQLTSEEDT

LTLVTADHSHVFSFGGYTLRGSSIFGLAPSKAQDSKAYTSILYGNGPGYV

FNSGVRPDVNESESGSPDYQQQAAVPLSSETHGGEDVAVFARGPQAHLVH

GVQEQSFVAHVMAFAACLEPYTACDLAPPACTTDAAHPVAASLPLLAGTL

LLLGASAAP

In some embodiments, a recombinant AP as described herein is employed in the invention. The AP variant displays enhanced stability and good selectivity for LPS (Kiffer-Moreira T, et al, PLoS ONE 2014; 9: e89374). This sequence is listed in SEQ ID NO 6.

SEQ ID NO 6:
VIPAEEENPAFWNRQAAEALDAAKKLQPIQKVAKNLILFLGDGLGVPTVT

ATRILKGQKNGKLGPETPLAMDRFPYLALSKTYNVDRQVPDSAATATAYL

CGVKANFQTIGLSAAARFNQCNTTRGNEVISVMNRAKQAGKSVGVVTTTR

VQHASPAGTYAHTVNRNWYSDADMPASARQEGCQDIATQLISNMDIDVIL

GGGRKYMFPMGTPDPEYPADASQNGIRLDGKNLVQEWLAKHQGAWYVWNR

TELMQASLDQSVTHLMGLFEPGDTKYEIHRDPTLDPSLMEMTEAALRLLS

RNPRGFYLFVEGGRIDHGHHEGVAYQALTEAVMFDDAIERAGQLTSEEDT

LTLVTADHSHVFSFGGYPLRGSSIFGLAPGKARDRKAYTVLLYGNGPGYV

LKDGARPDVTESESGSPEYRQQSAVPLDEETHGGEDVAVFARGPQAHLVH

GVQEQSFVAHVMAFAACLEPYTACDLAPPACTTD

In some embodiments the AP sequences employed are functionally equivalent to human, recombinant or bovine AP proteins as described herein, in other words, such functional equivalence is defined by the ability to dephosphorylate extracellular adenosine triphosphate (ATP), adenosine diphosphate (ADP), adenosine monophosphate (AMP) and/or lipopolysaccharide (LPS) in the blood of a patient in need thereof.

Variation in length of the amino acid sequences as described herein is also encompassed by the present invention. A skilled person is capable of providing amino acid sequence variants that are longer or shorter than SEQ ID NO 1, 2, 3, 4, 5 or 6, which will still exhibit sufficient similarity to the AP described herein in order to provide the outcomes desired. For example, shorter variants of SEQ ID NO 1, 2, 3, 4, 5 or 6 comprising 10, 20, 30, 40, 50 or up to 100 amino acids less than the full-length form may also enable effective target dephosphorylation, as described herein. Active fragments of AP are therefore also considered. Additionally, longer variants of SEQ ID NO 1, 2, 3, 4, 5 or 6 comprising 10, 20, 30, 40, 50 or up to 100 amino acids any given additional sequence more than the AP sequence may also enable effective outcomes, as described herein.

In other embodiments of the invention, the AP protein employed may comprise or consist of an amino acid sequence with at least 50%, 60%, 70%, 80%, 90% or 95% sequence identity to SEQ ID NO 1, 2, 3, 4, 5 or 6. Preferably the sequence variant comprises at least 80%, 90%, 91, 92, 93, 94, 95, 96, 97, 98 or 99% sequence identity to SEQ ID NO 1, 2, 3, 4, 5 or 6 and preferably exhibits functional analogy to the AP described herein. In preferred embodiments the AP protein employed comprises least 80%, 90%, 91, 92, 93, 94, 95, 96, 97, 98 or 99% sequence identity to SEQ ID NO 1, 2, 3, 4, 5 or 6.

In some embodiments, the invention covers any AP that is capable of dephosphorylating extracellular adenosine triphosphate (ATP), adenosine diphosphate (ADP), adenosine monophosphate (AMP) and/or lipopolysaccharide (LPS) in the blood of a patient, when immobilized on a membrane, support or other matrix as described herein.

"Dephosphorylating" as used herein relates to the removal of a phosphate ($PO_4^{3-}$) group from an organic compound, such as by hydrolysis. Phosphorylation is a reversible post-translational modification, which can be removed via dephosphorylation. Dephosphorylation and its counterpart, phosphorylation, typically activate and deactivate enzymes, or regulate signaling, by detaching or attaching phosphoric esters and anhydrides. A notable occurrence of dephosphorylation is the conversion of ATP to ADP and inorganic phosphate. Dephosphorylation employs a type of hydrolytic enzyme, or hydrolase, which cleave ester bonds. The prominent hydrolase subclass used in dephosphorylation is a phosphatase, as in AP. Phosphatase removes phosphate groups by hydrolysing phosphoric acid monoesters into a phosphate ion and a molecule with a free hydroxyl (—OH) group.

Membrane Materials and Hemofilters:

According to one aspect, the device is a hollow fiber membrane dialyzer which is designed for use in hemodialysis and wherein the lumen side of the hollow fibers of the hemodialyzer are functionalized with alkaline phosphatase (AP). According to one embodiment of the invention, the device according to the invention comprises hollow fiber membranes selected from a group of hemodialysis hollow fiber membranes prepared from polysulfone, polyethersulfone or polyarylethersulfone and polyvinylpyrrolidone.

A hollow fiber membrane which can advantageously be utilized for providing a device according to the invention preferably has an inner diameter in the range of 100 to 500 μm. According to one embodiment of the present invention the hollow fiber membrane has a wall thickness in the range of from 20 to 150 μm. Lower wall thicknesses are disadvantageous due to reduced mechanical properties of the fiber during production and during its use in the device according to the invention itself. Higher wall thicknesses are disadvantageous because they require increased time intervals to perform the phase inversion process resulting in instable process conditions and an instable membrane.

Polysulfone/PVP based membranes, including those prepared from PES or PAES, which can be used according to the invention, can be classified as "high-flux" (HF), "medium cut-off" (MCO) and "high cut-off" (HCO) membranes. All of these membranes have been described in the literature.

Their production, even though the same polymers are involved, is relevant for the defined properties these membranes have. Today, diffusion-induced phase separation processes are primarily used, which permit polymer combinations and the fine-tuning of pore size and diffusive-transport characteristics. The polymers are dissolved in a suitable solvent, and precipitation takes place in a non-solvent bath, preferably water. The concentration of the polymer in the polymer solution is approximately 20 wt %, depending on the particular recipe. The polymer solution is pumped through an annular die (spinneret) to form a hollow fiber. The inner void of the hollow fiber is formed by a bore liquid (a mixture of solvent and non-solvent), which is introduced into the inner part of the spinneret. In a third step, the hollow fiber is guided through a non-solvent bath. The non-solvent bath and bore liquid are required to convert the homogeneous liquid-polymer solution into a two-phase system via diffusive solvent/non-solvent exchange (immersion precipitation). The demixing process stops at the vitrification point of the polymer-rich phase. A rigid membrane structure is formed during the polymer-rich phase, and the membrane pores are formed during the liquid-polymer-poor phase. The major influences on membrane properties during the manufacturing process are composition, viscosity and temperature of the polymer solution, the use of additives, the ability to crystallize or aggregate, nozzle design, composition of the coagulation bath, the conditions between the nozzle and coagulation-bath entrance, specifically the temperature and the humidity in the spinning shaft, and potentially also finishing treatments such as drying and or sterilizing the membrane with heat or by irradiation (see, for example, Zweigart et al (2017) 4.11 Progress in the Development of Membranes for Kidney-Replacement Therapy. In: Drioli, E., Giorno, L., and Fontananova, E. (eds.), Comprehensive Membrane Science and Engineering, second edition. vol. 4, pp. 214-247. Oxford: Elsevier). The performance of the final fiber bundle and filter are otherwise influenced by undulation of the fibers, which provides them with a wavy geometry, as described in EP3010629. The final assembly of a filter is described in Zweigart et al., 2017. Membranes and filters according to the invention can be sterilized by several, generally known means. It will be advantageous to sterilize devices according to the invention by irradiation with gamma rays or e-beam. Both are standard techniques. The radiation dose for gamma ray sterilization is between 5 and 40 kGy. Steam sterilization can also be used and is the method of choice in terms of environmental impact and patient application. Despite the various methods of producing membranes available, a skilled person is capable of selecting and manufacturing an appropriate membrane without undue effort.

According to one aspect of the invention, the blood purification device comprises high-flux membranes on which AP has been immobilized. High-flux membranes used in devices, such as, for example, Polyflux® 170H (Baxter), Revaclear® (Baxter), Ultraflux® EMIC2 (Fresenius Medical Care), or Optiflux® F180NR (Fresenius Medical Care) have been on the market for several years. Methods for their production have been described, for example, in U.S. Pat. No. 5,891,338 and EP2113298. Another known membrane is used in the Phylther® UP series from Bellco. These products are based on polyphenylene. In polysulfone or polyethersulfone based membranes as referred to in this application, the polymer solution generally comprises between 10 and 20 weight-% of polyethersulfone or polysulfone as hydrophobic polymer and 2 to 11 weight-% of a hydrophilic polymer, in most cases PVP, wherein said PVP generally consists of a low and a high molecular PVP component. The resulting high-flux type membranes generally consist of 80-99% by weight of said hydrophobic polymer and 1-20% by weight of said hydrophilic polymer. During production of the membrane the temperature of the spinneret generally is in the range of from 25-55° C. Polymer combinations, process parameters and performance data can otherwise be retrieved from the references mentioned or can be taken from publicly available data sheets. The expression "high-flux membrane (s)" as used herein otherwise refers to membranes having a MWRO between 5 kDa and 10 kDa and a MWCO between 25 kDa and 65 kDa, as determined by dextran sieving measurements according to Boschetti-de-Fierro A et al. (Extended characterization of a new class of membranes for blood purification: The high cut-off membranes. Int J Artif Organs 2013; 36(7), 455-463). The average pore radius before blood contact is in the range of from 3.5 to 5.5 nm, wherein the pore size is determined from the MWCO based on dextran sieving coefficients according to Boschetti-de-Fierro et al. (2013).

According to one aspect of the invention, the blood purification device comprises high cut-off membranes on which AP has been immobilized. This type of membrane has first been disclosed in WO 2004/056460 wherein certain early high cut-off membranes are described, which were already primarily intended for the treatment of sepsis by eliminating sepsis-associated inflammatory mediators. Advanced dialyzers making use of high cut-off type membranes which are currently on the market are, for example, septeX and Theralite (Baxter). Known uses of said advanced high cut-off membranes include treatment of sepsis (EP2281625), chronic inflammation (EP2161072), amyloidosis and rhabdomyolysis and treatment of anemia (US2012/0305487), the most explored therapy to date being the treatment of myeloma kidney patients (U.S. Pat. No. 7,875,183 B2). Accordingly, these membranes and filters are already well adapted to being used in acute settings and therefore especially useful in treatments according to the invention. The expression "high cut-off membrane" or "high cut-off membranes" as used herein refers to membranes having a MWRO of between 15 and 20 kDa and a MWCO of between 170-320 kDa. The membranes can also be characterized by a pore radius, on the selective layer surface of the membrane, of between 8-12 nm before blood contact. For the avoidance of doubt, the determination of MWRO and MWCO for a given membrane and as used herein is according to the methods of Boschetti-de-Fierro et al. (2013). Processes for producing high cut-off membranes have been described, for example, in the aforementioned references. As disclosed already in WO 2004/056460, a key element for their generation is a careful control of the temperature of the spinning process, i.e. the temperature of the spinneret, the spinning shaft temperature and temperature of the coagulation bath, relative to the spinning conditions for producing a high-flux membrane with about the same composition of polymers. In addition, for the production of the latest high cut-off membranes such as the Theralite membrane, the ratio of water and solvent ($H_2O$/solvent) in the polymer solution is also slightly changed to lower values while the polymer content in said solution can otherwise be similar to or the same as used for producing high-flux membranes such as, for example, the Revaclear membrane. For the avoidance of doubt, the MWCO and MWRO values used for describing the prior art membranes and the membranes according to the invention have been measured before blood or plasma contact, because the sieving properties of synthetic membranes may change upon such contact.

According to one aspect of the invention, the blood purification device comprises medium cut-off membranes on which AP has been immobilized. MCO membranes and filters comprising same and methods for producing them have been described in detail in WO 2015/118045 A1, WO 2015/118046 A1 and, for example, in Zweigart et al. (2017). The first dialyzer on the market comprising such MCO membranes is Theranova (Baxter). Said medium cut-off membranes and dialyzers fills the gap in performance between high-flux and high cut-off dialyzers. The expression "medium cut-off membranes" as used herein, refers to membranes having a molecular retention onset (MWRO) of between 9.0 kDa and 14.0 kDa and a molecular weight cut-off (MWCO) of between 55 kDa and 130 kDa as determined by dextran sieving curves before the membrane has had contact with blood or a blood product. Due to this very unique sieving profile the membranes considerably extend the performance of current high-flux membranes and dialyzers, as they allow for the removal of middle and large uremic solutes which cannot be addressed by the current high-flux membranes. They are, therefore, also referred to as "membranes with increased permeability". At the same time, such membranes are able to address such higher molecular weight compounds without having to face unacceptable albumin losses during treatment. As a consequence, these membrane types can be used in both acute and chronic settings. For the avoidance of doubt, the expression "membrane(s) with increased (or "extended") permeability" as used herein is equivalent with the expression "medium cut-off membrane".

According to yet another embodiment of the invention, the blood purification device comprises polyacrylonitrile (PAN) membranes comprising i) a copolymer of acrylonitrile and sodium methallyl sulfonate, ii) a polyethyleneimine, and iii) heparin on which AP has been immobilized. Polyacrylonitrile was the first synthetic material developed for dialysis membranes. The material of the old AN69 membrane developed by Hospal is a copolymer of acrylonitrile and sodium methallyl sulfonate. This combination is important and includes the addition of sodium methallyl sulfonate, which heavily influences membrane structure. These membranes are particularly useful for the treatment of sepsis or sepsis-induced acute kidney failure, in particular for adsorbing endotoxins contained in the biological fluid, for purifying certain molecules contained in the blood or the plasma, i.e. via dephosphorylation of the target molecules described herein, and/or by extracorporeal circulation and for reducing systemic anticoagulation in a patient during an extracorporeal blood or plasma treatment.

A method for preparing a suitable membrane is also described in WO 2007/148147 A1. In one embodiment of the extracorporeal blood circuit, the membranes of the blood treatment device comprise polyethyleneimine in an amount of from 10 to 100 mg, for instance, from 25 to 50 mg per $m^2$ of membrane surface area, and from 1,500 to 10,000 UI, for instance, 3,000 to 6,000 UI, e.g. 4,500±1,500 UI, of heparin per $m^2$ of membrane surface area. In one embodiment, the blood treatment device comprises hollow fiber membranes having an inner diameter in the range of from 180 to 260 μm, e.g. 210 μm, or 240 μm. In one embodiment, the wall strength of the hollow fiber membranes is in the range of from 30 to 60 μm, e.g., 40 to 50 μm. In one embodiment, the overall surface area of the membranes in the diffusion- and/or filtration device is in the range of from 1 to 3 $m^2$, for instance, 1.0 to 2.2 $m^2$. In one embodiment, the hollow fiber membranes in the diffusion- and/or filtration device show sieving coefficients, measured at 37° C. in bovine plasma having a protein content of 60 g/l, of >0.95 for inulin; >0.55 for myoglobin; and <0.01 for albumin. The membranes in the diffusion- and/or filtration device have the ability to immobilize inflammatory mediators and endotoxins to their surface by adsorption. In one embodiment, the clearance rate for IL-6 in HDF mode with QB=400 ml/min, QD=700 ml/min and UF=100 ml/min is in the range of from 20 to 40 ml/min. PAN membranes exhibit a high adsorption capacity for proteins, including beta2-microglobulin, cytokines, and endotoxins, which makes them especially useful for use in acute therapies, such as CRRT, and specifically for treating sepsis induced AKI, even though there is a huge need to improve the clinical outcome of sepsis treatment with this membrane type.

Certain drawbacks of the membrane which existed in the early days of development are today overcome by coating the membrane surface with polycationic polyethylenimine, which has the additional benefit of binding heparin, thus permitting the administration of a lower heparin dosage during dialysis, which is a significant advantage in critically ill patients. Today, this membrane is available as AN69ST and used in commercial dialyzers such as, for example, Evodial and oXiris, which are known for use in CRRT. AN69 membranes are very well suited for covalently binding any type of protein, e.g. ligand or enzyme, which can be used to modify the activity or composition of a biological fluid (see, for example, U.S. Pat. No. 6,260,715 B1). This property of the membrane can advantageously be used for preparing a device according to the invention, by immobilizing AP on said membrane.

According to yet another aspect, wherein the membranes have a pore size which allows for the passage of larger proteins, e.g., a plasma separation membrane such as described in WO 2008/003610 A1, the outer surface and/or the pores of the hollow fiber membrane are functionalized with AP. Alternatively, only the lumen side of such plasma separation hollow fiber membranes is functionalized with AP.

According to yet another aspect, the device can be a hemodialyzer for the treatment of renal failure wherein the filter further comprises, in at least one of the end caps, a resin, e.g. in sponge form, or a non-woven, which is functionalized with AP.

Patients can be treated with devices according to the invention either intermittently or continuously. Continuous therapy is used exclusively for acute renal failure (ARF). Benefits over intermittent therapy include improved tolerability resulting from the slower removal of solutes and water. The treatment is performed in hemodialysis mode at blood flows between 200 and 500 mL/min.

In one embodiment of the invention, wherein the membrane used for providing a device according to the invention is a plasma separation membrane or is otherwise configured to allow the passage of the target according the invention to a significant amount with a sieving coefficient of higher than 0.5 and preferably higher than 0.7 or higher than 0.9, the inner layer or lumen of the hollow fibers which generally is the blood contacting layer, is not functionalized and does not carry any AP. The AP is instead coupled via a linker to the outer layer of the hollow fibers, and optionally also to at least a portion of the layer connecting the inner layer with the outer layer, i.e. the pores of the membrane. Accordingly, the functionalization with AP is present only on the outer filtrate layer and optionally on at least a portion of the pore surface structures connecting the outer and inner layer of the membrane. Such configuration can be applied, for example, for dephosphorylation of targets in whole blood which due to their size are able to pass from the inner layer to the outer layer, while larger blood proteins remain on the lumen side of the membrane. As blood components including the targets are passaging to the outer layer of the membrane they are modified (dephosphorylated) by AP.

Adsorber Materials and Adsorber Cartridges:

The device can also be an adsorption cartridge comprising a matrix selected from a resin or non-woven material, either of which is functionalized with AP. Such device can be a member of an extracorporeal circuit for blood treatment, configured to provide hemodialysis, hemodiafiltration, hemofiltration or plasmapheresis. The device can be the sole blood treatment device within the blood circuit or can be located, for example, upstream or downstream of the dialyzer in a hemodialysis, hemodiafiltration or hemofiltration circuit or can alternatively be immediately connected to the dialyzer at the blood inlet or outlet, wherein the device is configured to be perfused with whole blood. The device can also be a member of an extracorporeal plasmapheresis circuit, wherein the device is perfused with blood plasma or components thereof. The device can also be used in therapeutic plasma exchange (TPE) treatment, wherein the plasma is removed from the patient and is then replaced with a substitute, e.g. fresh frozen plasma.

The device can also be a hybrid filter device which combines hollow fiber membranes and a matrix in the filtrate space of the filter, as described in (WO 2014/079680 A1). In the present invention, the matrix consists of a resin which is functionalized with AP for dephosphorylating the targets described herein. Such filter can be a member of an extracorporeal circuit configured for performing hemodialysis, hemodiafiltration or hemofiltration, wherein the said filter is located either upstream or downstream of the dialyzer for hemodialysis, hemodiafiltration or hemofiltration, or it can be used as a sole filter device within the said circuit in the absence of such dialyzer. Such device can be used with whole blood.

Extracorporeal devices and methods for removing target components from the blood of a patient have been described before. For example, WO 2013/020967 A1 discloses the use of a device and matrix for the immobilization and removal of blood group antibodies from a patient. U.S. Pat. No. 8,969,322 B2 described an extracorporeal apheresis procedure for the removal of soluble Flt-1 receptor from the blood of a patient by means of a device comprising dextran sulfate. In analogy to these approaches, the present invention employs immobilization of AP to a blood treatment device and its suitability in treating infection, such as sepsis, and renal failure, preferably SA-AKI.

Accordingly, in one aspect, the invention discloses devices comprising a matrix which is designed for the specific dephosphorylating of extracellular adenosine triphosphate (ATP), adenosine diphosphate (ADP), adenosine monophosphate (AMP) and/or lipopolysaccharide (LPS) in the blood of a patient. According to another aspect, the invention discloses extracorporeal circuits comprising said devices and describes how such circuits should be configured to effectively treat the blood of the patient in need. According to yet another aspect, the invention provides for a method for reducing the level of extracellular adenosine triphosphate (ATP), adenosine diphosphate (ADP) and/or phosphorylated lipopolysaccharide (LPS) in the blood of a patient, comprising the step of extracorporeally removing the target proteins from the patient by passing the blood or the blood plasma of the patient through a device according to the invention.

According to one aspect, the device according to the invention comprising an adsorbent, e.g. in the form of beads, has an active surface are, per device, in the range of between 0.5 and 50000 $m^2$ when used in whole blood perfusion (hemoperfusion). According to another aspect, the said device according to the invention has an active surface are, per device, in the range of between 0.5 and 50000 $m^2$ when used in whole plasma perfusion (therapeutic apheresis). According to yet another aspect, the said devices for hemoperfusion and/or whole plasma perfusion have an active surface area, per device, in the range of between 0.5 and 10000 $m^2$.

The expression "matrix" as used herein thus refers to a material which can be used for immobilizing AP according to the invention. Such matrix as used in the context of the present invention may in some embodiments comprise a support to which AP is bound. The support therefore serves as a carrier for AP, even though it has to fulfil other functions as well.

According to one specific embodiment of the invention, the AP comprises affinity tags for immobilizing it on the support. Affinity tags can be used for purifying the protein during their production and/or for immobilizing them on the support of the matrix of the present invention. Affinity tags can be short polypeptide sequences or whole proteins, co-expressed as fusion partners with the target proteins. Apart from facilitating purification and quick immobilization, fusion tags are sometimes also advantageous in increasing the expression and solubility of recombinant proteins. Affinity tags can be used to ensure proper orientation of the protein, or various orientations can be used, thus, making the functional domains accessible for interaction. Different types of affinity tags are well known in the art (Terpe, Appl Microbiol Biotechnol (2003) 60:523-533), wherein polyhistidine or $His_6$-tags are especially well described and are one option for binding AP according to the invention to the support material. Affinity tags which can otherwise be used for binding AP to the support can be selected from the group comprising C-myc-tags, FLAG-tags, and Hemagglutinin (HA)-tags.

According to another embodiment of the invention, AP protein can also be immobilized onto supports by using a secondary ligand to adsorb the AP. This can be accomplished by using AP that has been reacted with biotin or biotinylated, and then adsorbed to a support that contains immobilized avidin or streptavidin. One possible biotinylation technique is to incubate AP with N-hydroxysuccinimide-D-biotin at pH 9. The noncovalent linkage of biotin to streptavidin or avidin can then be used to immobilize these proteins. These linkages have association equilibrium constants in the range of $10^{13}$-$10^{15}$ $M^{-1}$.

According to another embodiment of the invention, the AP protein is covalently attached to the support as further detailed below and/or as described the prior art (Cuatrecasas, J Biol Chem (1970) 245:3059-3065; Nisnevitch et al., J Biochem Biophys Methods (2001) 49:467-480). Covalent coupling generally includes either covalent non-site directed attachment of the protein which is based on utilizing functional groups on either the support and/or the protein (Nisnevitch et al., J Biochem Biophys Methods (2001) 49:467-480, Section 2.3). According to another embodiment of the invention the covalent attachment of proteins is a site-directed attachment of the protein (Nisnevitch et al., J Biochem Biophys Methods (2001) 49:467-480, Section 2.4; Makaraviciute et al., Biosensors and Bioelectronics (2013) 50:460-471). Essentially, technical guidance for attaching an antibody to a matrix, as is typically carried out in immunoaffinity approaches, may be applied to immobilize AP protein on the support. References disclosed herein regarding antibody immobilization to a support or matrix are also considered potentially relevant for immobilizing monomeric AP variants.

The expression "support" as used herein refers to the portion of the matrix which serves as the "substrate" or "support material" to which AP according to the invention is bound. Such support or support material is sometimes also referred to as "adsorption material" or "adsorber" and such expressions shall be encompassed by the expression "support" as used herein.

In other embodiments, references to "support", for example when referring to immobilization methods for immobilizing AP, also apply to membranes, such as those of the hemofilters disclosed herein.

A suitable support according to the present invention should be uniform, hydrophilic, mechanically and chemically stable over the relevant pH range and temperature with no or a negligible leaching of AP during use, selective, exhibit minimum non-specific absorption, and should otherwise be blood compatible, i.e. does not induce adverse reactions including the activation of the complement system or other immunological pathways, has good flow characteristics for whole blood and/or blood plasma, and provides a large surface area for AP attachment.

The support can be a resin, a membrane or a non-woven. The expression "resin" as used herein, refers to an insoluble material which can take the form of translucent gels or gel beads or microporous beads having pores and an opaque appearance, or can take the form of a sponge. Such resins can be natural or bio-polymers, synthetic polymers and inorganic materials. Agarose, dextrose and cellulose beads are commonly employed natural supports. Synthetic polymeric or organic supports are mostly based on acrylamide, polystyrene and polymethacrylate derivatives, whereas, porous silica and glass are some frequently used inorganic supports. Other materials which can be used in accordance with the invention are described below.

According to one embodiment of the invention, the resin is composed of polymers selected from the group consisting of alginate, chitosan, chitin, collagen, carrageenan, gelatin, cellulose, starch, pectin and sepharose; inorganic materials selected from the group consisting of zeolites, ceramics, celite, silica, glass, activated carbon and char-coal; or synthetic polymers selected from the group consisting of polyethylene (PE), polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), polyacrylate (PAA), polymethyl methacrylate (PMMA), polyacrylamide, polyglycidyl methac-rylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), eth-ylene vinyl acetate (EVA), ethylene vinyl alcohol (EVOH), polyamideimide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allylbenzoic acid), poly(glycidyl acrylate), polyglycidyl methacrylate (PGMA), acrylonitrile butadiene styrene (ABS), polydivinylbenzene (PDVB), poly(allyl glycidyl ether), poly (vinyl glycidyl ether), poly(vinyl glycidyl urethane), polyallylamine, polyvinylamine, copolymers of said polymers and any of these polymers modified by introduction of functional groups. According to one specific embodiment of the invention, the support is selected from the group consisting of styrene divinylbenzene (DVB) and derivatives, polymethyl methacrylate (PMMA) and derivatives, and polyglycidyl methacrylate (PGMA) and derivatives.

According to yet another embodiment of the invention, the support is a non-woven. The expression "non-woven" as used herein refers to a material which is broadly defined as a sheet, fabric or web structure bonded together by entangling fiber or filaments (and by perforating films) mechanically, thermally, or chemically but not by weaving or knitting. They form porous structures which can efficiently be used as a support material in devices according to the invention due to their high filtration efficiency, high surface area and high permeability. Non-wovens and processes for their production, comprising melt-blown non-wovens and spunlaid nonwovens, as well as devices containing such non-wovens are known in the art and have been described, for example, in EP 1 922 097 A1, WO 2007/025738 A2 and in Zhao et al., J Mem Sci (2011), 369: 5-12. Non-wovens can be composed of biopolymers selected from the group consisting of polysaccharides, polylactic acids (PLA), polycaprolactone (PCL) and proteins, from inorganic materials selected from the group consisting of $TiO_2$, $SiO_2$ or $AlO_2$, or from synthetic polymers selected from the group consisting of polypropylene(PP), polyethylene(PE), polyacrylonitrile (PAN), Poly(vinyl alcohol)(PVA), polyamide-imide (PAI), polyurethane (PUR), polyethersulfone (PES), polyacrylic acid (PAA), polyethylene oxide (PEO), polystyrene (PS) and polyvinylidene fluoride (PVDF).

According to another aspect, the device according to the invention can be a filter device as disclosed in WO 2014/07680 A1, which comprises both a bundle of hollow fiber membranes and a resin in the filtrate space of the device, wherein the resin preferably consists of beads. Such device can be configured in a way to serve as a device for dephosphorylating a target according to the present invention by selecting a membrane which allows the passage of at least the relevant targets through the membrane wall. The resin in the filtrate space of the device serves as the matrix and comprises a resin support, such as disclosed herein or in WO 2014/07680 A1, to which the AP is bound by methods disclosed herein or as otherwise known in the art.

Immobilization of AP:

As mentioned above, AP according to the invention may be covalently bound to the support or membrane. In this context, references to a support of the matrix may also apply to the membrane of a hemofilter, depending on the particular material of the membrane and applicability to the immobilization strategy employed.

The support which forms the basis for the generation of a matrix wherein the AP can be attached covalently must provide or facilitate chemical activation, thus allowing the chemical coupling of the AP. Many coupling methods for immobilizing other ligands, such as antibodies or fragments thereof, are well known in the art and may be employed for immobilizing AP. In general, the activation chemistry should be stable over a wide range of pH, buffer conditions and temperature resulting in negligible leaching of the bound protein or ligand (in this case AP). The coupling method should avoid improper orientation, multisite attachment or steric hindrance of AP, which may cause masking of the active enzymatic sites or pockets and, subsequently, lead to loss of activity. Site-directed attachment and/or spacers can be considered for immobilizing the AP onto the support. The AP density per volume of matrix can be optimized to promote target accessibility and activity.

The coupling can be carried out via common functional groups, including amines, alcohols, carboxylic acids, aldehydes and epoxy groups (FIGS. 6A and 6B). Methods of preparing supports according to the invention are known in the art and are described, for example, in U.S. Pat. No. 8,142,844 B2, US 2015/0111194 A1 and US 2014/0166580 A1. These references also describe spacer groups (or "linker" groups) which can be used in generating the matrix according to the invention.

According to one embodiment of the invention, the AP is coupled directly or under addition of a spacer via an amine function. In a first step, an amine group is introduced onto the support. Many methods can be used for introducing amine groups to substrates according to the invention. For example, addition of aminated polymers (e.g. aminated polyvinylalcohols) to the polymer solution prior to membrane precipitation, or post-treatment of membranes such as silanization of a membrane containing hydroxyl or/and carboxyl groups using APTMS ((3-aminopropyl)trimethoxysilane-tetramethoxysilane), simple adsorption of PEI (poly (ethylene imine)) or other polymers onto the membrane surface, or plasma treatment of the membranes with ammonium or other organic amine vapors can effectively be used to introduce amine groups onto membranes. In a second step, carbodiimide compounds can be used to activate carboxylic groups of proteins for direct conjugation to the primary amines on the membrane surface via amide bonds. The most commonly used carbodiimides are the water-soluble EDC (1-ethyl-3-(3-dimethylaminopropyl) carbodiimide) for aqueous crosslinking and the water-insoluble DCC (N',N'-dicyclohexyl carbodiimide) for non-aqueous organic synthesis methods. According to another embodiment of the invention, hydroxyl groups can be introduced to the support. Substrates based on polysaccharides, for example cellulose or cellulose derivatives, already carry OH-groups on the surface. Hydroxy groups can also be introduced to the substrate for example by plasma treatment with oxygen or air. After acylation of the hydroxy group with succinic anhydride the resulting O-succinate can react with amine of the protein with amide bond formation in the presence of carbodiimide or other coupling reagents. According to yet another embodiment of the invention, carboxylic acid groups can be introduced to the support. Carboxylate groups can be introduced on substrates by plasma treatment with carbon dioxide. For protein immobilization carbodiimide/succinimide coupling chemistry can be used for surface attachment via amine group of the AP. According to yet another embodiment of the invention, carbonyl groups (aldehydes, ketones) can be introduced for the subsequent coupling of AP. Aldehydes can be created on polysaccharide-based solid substrates by oxidation of OH-groups using periodic acid. The primary amines of proteins (N-terminus of polypeptides and the side chain of lysines) can react with aldehydes via reductive amination and formation of a Schiff base. The Schiff base formed then hydrolyzes in an aqueous solution and must be reduced to an alkylamine linkage for stabilization. Sodium cyanoborohydride is a mild reducing agent that induces this reaction without also reducing other chemical groups of proteins. According to still another embodiment of the invention, epoxy groups can be introduced to a support. Several pre-activated resins coated with high density epoxy functional groups on the surface are available commercially, see below. The introduction of epoxy groups on membranes is described, for example, in WO 2005/026224 A1. The epoxide group which reacts with nucleophiles in a ring-opening process reacts with primary amines, thiols or hydroxyl groups of proteins to form stable secondary amines, thioesters and ether bonds, respectively. The epoxide groups readily react with thiol groups and require buffered systems close to physiological pH (pH 7.5-8.5). The epoxide groups require high pH conditions (pH 11-12) for reacting with hydroxyl groups and moderate alkaline conditions (pH>9) for reaction with amine groups. In each case, spacers of varying chain length can be introduced between the support and the AP.

There are several types of supports as mentioned above and below that can be advantageously utilized to couple, for example, proteins for use in affinity chromatography. Affinity supports can be based on materials such as polysaccharide. Suitable polysaccharides are, for example, cellulose, nitrocellulose, chitosan, collagen, starch and cross-linked polysaccharide gels such as agarose, Sephadex or Sepharose. Methods for preparing derivatives of polysaccharide matrices have long been known and are, for example, described in U.S. Pat. No. 4,411,832 or U.S. Pat. No. 3,947,352. The supports can also be based on synthetic organic supports. Synthetic polymeric matrices comprise hydrophilic and hydrophobic synthetic polymers and combinations thereof. Synthetic supports comprise supports selected, for example, from the group of supports consisting of polyacrylamide supports or derivatives thereof; polymethacrylate supports or derivatives thereof; polystyrene supports or derivatives thereof; or polyethersulfone supports or derivatives thereof. Otherwise, derivatized silica, glass or azlactone beads can be used in devices according to the invention. Such devices preferably make use of organic supports. The use of beads may be advantageous in the context of the present invention.

According to one embodiment of the invention, the support material should be porous, wherein the pore size is in the range of from 10 to 200 nm. For affinity applications the pore size has been found to be optimal in the range of from 30 to 200 nm or in the range of 60 to 200 nm. However, other pore sizes may be advantageous as well depending on the coupling chemistry, spacer and AP type used, and also depending on the targets for dephosphorylation. If the support is used in the form of beads, the diameter of such beads may vary of a certain range. It may be advantageous to use beads with a diameter in the range of from 50 to 1000 µm. It may be further advantageous to use beads with a diameter in the range of from 60 to 800 µm, 100 to 700 µm, 120 to 800 µm.

According to one aspect of the present invention, the supports carry specific functional groups which are needed for coupling a linker and/or AP thereto. For example, many functionalized resins are commercially available and known to a person with skill in the art. Pre-activated resin supports which already carry a reactive group for the coupling of AP with or without a spacer are available commercially and eliminate many of the steps of chemical activation of the support prior to use mentioned before, i.e. prior to the coupling of AP. Such supports are generally resins as defined before, whereas for membrane and/or non-woven supports the step of activation generally has to be performed before coupling. A wide range of coupling chemistries, involving primary amines, sulfhydryls, aldehydes, hydroxyls and carboxylic acids are available in said commercial supports for covalently attaching AP. Examples for commercially available activated resins are UltraLink Iodoacetyl resin, Carbo-Link Coupling resin, Profinity™ Epoxide resin, Affi-Gel 10 and 15, Epoxy-activated Sepharose™ 6B, Tresyl chloride-activated agarose, Tosoh Toyopearl® AF Amino or Epoxy 650-M, ChiralVision Immobead™ 350, Resindion ReliZyme™ EXE 135 or SEPABEADS™ and Purolite® Lifetech™ methacrylate polymers functionalized with epoxy groups.

According to one embodiment of the invention, the support used for the coupling of AP is epoxy functionalized because epoxy groups form very stable covalent linkages with different protein groups such as, for example, —$NH_2$ in lysine or nucleophiles (amino, thiol, phenolic) and immobilization can be performed under mild conditions of pH and temperature.

According to another embodiment of the invention, the support takes the form of beads. According to yet another embodiment of the invention, the support is an epoxy-functionalized methacrylate polymer. According to yet another embodiment of the invention, the support is selected from the group of supports consisting of Tosoh Toyopearl® Epoxy 650-M, ChiralVision Immobead™ 350, Resindion ReliZyme™ EXE 135, Resindion SEPABEADS™ and Purolite® Lifetech™. According to one aspect, Purolite® Lifetech™ ECR8209F epoxy methacrylate beads are used which carry an epoxy group as a functional group to which AP can be bound. They have a mean pore diameter of between 1200 and 1800 Å and a particle size of between 150 and 300 µm. According to another aspect, Purolite® Lifetech™ ECR8215M epoxy methacrylate beads are used which carry an epoxy group as a functional group to which AP can be bound. They have a mean pore diameter of between 600 and 1200 Å and a particle size of between 300 and 710 µm. According to another aspect, Purolite® Lifetech™ ECR8215F epoxy methacrylate beads are used which carry an epoxy group as a functional group to which AP can be bound. They have a mean pore diameter of between 1200 and 1800 Å and a particle size of between 150 and 300 µm.

According to another embodiment of the invention, it is also possible to immobilize the AP non-covalently to the support, for example ionically or by complexation. However, covalent binding is preferred to avoid the risk of leaching of AP from the matrix into the blood or blood plasma of the patient.

According to another embodiment of the present invention the support is a membrane. According to one embodiment of the invention, the support membrane is a hollow fiber membrane. According to another embodiment of the invention, a multitude of hollow fiber membranes are formed to a bundle of hollow fibers and embedded in a housing, thus forming a filter or filtration device. According to one embodiment, the support comprises a hemodialysis hollow fiber membrane dialyzer, wherein the filter is a hemodialyzer, or hemofilter.

The hollow fiber or flat sheet membranes for use as supports in a device according to the invention may be composed of cellulose, cellulose ester (cellulose acetate and cellulose triacetate), poly(methylmethacrylate)(PMMA), polyamide (PA), other nitrogen-containing polymers (polybenzimidazole, polyacrylonitrile (PAN), polyglycidyl methacrylate (PGMA), polyvinylpyrrolidone (PVP), polysulfone (PS), polyethersulfone (PES), polyarylethersulfone (PAES), combinations of said polymers and any of these polymers modified by introduction of functional groups. According to one embodiment of the invention, the membrane supports according to the invention comprise a polymer selected from the group of polymers consisting of poly(methylmethacrylate) (PMMA), polyamide (PA), polyacrylonitrile (PAN), polyvinylpyrrolidone (PVP), polysulfone (PS), polyethersulfone (PES), polyarylethersulfone (PAES), combinations of said polymers and any of these polymers modified by introduction of functional groups. According to another embodiment of the invention, the membrane supports according to the invention comprise a polymer selected from the group of polymers consisting of polyamide (PA), polyacrylonitrile (PAN), polyvinylpyrrolidone (PVP), polysulfone (PS), polyethersulfone (PES), polyarylethersulfone (PAES), combinations of said polymers and any of these polymers modified by introduction of functional groups. According to yet another embodiment of the invention, the membrane supports according to the invention comprise a polymer selected from the group of polymers consisting of polyvinylpyrrolidone (PVP), polysulfone (PS), polyethersulfone (PES), and polyarylethersulfone (PAES), combinations of said polymers and any of these polymers modified by introduction of functional groups.

For performing a coupling reaction for the subsequent binding of AP on the membrane surface, a polymer functionalization step is needed known methods can be used such as described in, for example, US 2015/0111194 A1 and US 2014/0166580 A1. For example, a synthetic material made of an alkane chain like, e.g., polyethylene, does not comprise suitable functional groups for coupling a molecule thereto. Therefore, suitable functional groups have to be introduced chemically after polymer synthesis. A possibility for modifying a polymer is the known method of plasma functionalization which allows, by selection of suitable gas plasma, to introduce functional groups into polymers. This method comprises, for example, the use of ammonia plasma, wherein amino functions are formed on the surface of the treated polymer. Hence, treatment of e.g. polyethylene with ammonia plasma leads to a polyethylene matrix bearing a certain amount of amino functions. These amino groups may afterwards be reacted with a suitable functional group of the linker, e.g. a carboxyl group. Alternatively, the matrix polymer can be functionalized by plasma activation to obtain carboxylic groups. A method for functionalizing a hollow fiber membrane in a continuous manner is further described, for example, in US 2007/0296105 A1. In said method the functional groups comprised introduced by the precursor gas may be amino, carboxyl, aldehyde, ester, epoxy, hydroxyl or sulphonic acids groups. Membranes which can be used as supports according to the invention comprise, for example, plasma separation membranes and hemodialysis membranes known in the art, including, but not limited to, well known high-flux membranes, high cut-off membranes or medium cut-off membranes. It is the goal of plasma separation to have the total plasma protein of the blood in the separated plasma fraction, whereas the larger corpuscular components of the blood, like blood cells and cell debris, are retained by the membrane. Further, such a plasma separation membrane should exhibit a high surface porosity and total porosity of the membrane to achieve high filtration performance. It should also be characterized by a hydrophilic, spontaneously wettable membrane structure, low fouling properties for long term stable filtration, and low protein adsorption. Such a plasma separation membrane preferably has smooth surfaces in contact with blood, thus avoiding or minimizing hemolysis during blood processing. The membrane should show constant sieving properties and filtration behavior over the whole treatment period. It should further exhibit high biocompatibility, low or no complement activation and low thrombogenicity. Membranes suitable for plasma separation which can be used for providing a device according to the invention are known in the art and have been described, for example, in EP 1 875 956 A1 or EP 1 875 957 A1. Other membranes which can be modified and used as supports in devices according to the invention, such as high-flux membranes as used, for example, in the Revaclear® dialyzer, have been described in EP 2 113 298 B1. Medium cut-off membranes as used, for example, in the Theranova® dialyzer have been described US 2017/0165616 A1 and high cut-off membranes as used, for example, in the Theralite® dialyzer, have been described in EP 1 572 330 A1.

Medical Use, Infection and Sepsis:

In some embodiments, the present invention relates to the blood treatment device as described herein for use as a medicament in the treatment of an infection, preferably a blood or systemic infection. In some embodiments, any infection may be treated that is associated with phosphorylated LPS, or ATP or ADP. Corresponding methods of treatment are also envisaged.

As used herein, "infection" within the scope of the invention means a pathological process caused by the invasion of normally sterile tissue or fluid by pathogenic or potentially pathogenic agents/pathogens, organisms and/or microorganisms, and relates preferably to infection(s) by bacteria, viruses, fungi, and/or parasites. Accordingly, the infection can be a bacterial infection, viral infection, and/or fungal infection. The infection can be a local or systemic infection. For the purposes of the invention, a viral infection may be considered as infection by a microorganism.

Further, the subject suffering from an infection can suffer from more than one source(s) of infection simultaneously. For example, the subject suffering from an infection can suffer from a bacterial infection and viral infection; from a viral infection and fungal infection; from a bacterial and fungal infection, and from a bacterial infection, fungal infection and viral infection, or suffer from a mixed infection comprising one or more of the infections listed herein, including potentially a superinfection, for example one or more bacterial infections in addition to one or more viral infections and/or one or more fungal infections.

As used herein "infectious disease" comprises all diseases or disorders that are associated with bacterial and/or viral and/or fungal infections. Diseases to be treated include, in some embodiments, all infectious diseases associated with phosphorylated LPS, or ATP or ADP, or which would benefit from treatment with an immobilized AP as described herein.

Subjects undergoing treatment according to the present invention may also undergo additional treatment for the infection. A medical treatment of the present invention may be an antibiotic treatment, wherein one or more "antibiotics" or "antibiotic agents" may be administered if an infection has been diagnosed or symptoms of an infectious disease have been determined. Further antibiotic agents/treatments or therapeutic strategies against infection or for the prevention of new infections include the use of antiseptics, decontamination products, anti-virulence agents like liposomes, sanitation, wound care, surgery. It is also possible to combine several of the aforementioned antibiotic agents or treatments strategies with fluid therapy, platelet transfusion or transfusion of blood products.

In preferred embodiments of the present invention the patient has been diagnosed as suffering from sepsis. In some embodiments, the patient may have been diagnosed as suffering from severe sepsis and/or septic shock.

A significant number of patients in intensive care units die from a complication known commonly as "sepsis" or "septic shock". Sepsis is the body's overwhelming and life-threatening response to infection that can lead to tissue damage, organ failure, and death. General parameters for sepsis are fever (core temperature >38.3° C.), hypothermia (core temperature <36° C.), heart rate >90 bpm or >2 SD above the normal value for a given age, tachypnea: >30 bpm and altered mental status, as well as significant edema or positive fluid balance (>20 mL kg−1 over 24 h) and hyperglycemia (plasma glucose >110 mg dL−1 or 7.7 mM L−1) in the absence of diabetes. Sepsis progresses to severe sepsis when in addition to signs of sepsis, there are signs of organ dysfunction, such as difficulty breathing (problems with the lungs), low or no urine output (kidneys), abnormal liver tests (liver), and changes in mental status (brain). Nearly all patients with severe sepsis require treatment in an intensive care unit (ICU).

Septic shock is the most severe level and is diagnosed when blood pressure drops to dangerous levels. In addition, trauma, burns, pancreatitis and ischaemia-reperfusion injury are among the non-infection causes of SIRS, the systemic inflammatory response syndrome, multiorgan system dysfunction syndrome ("MODS"), and multiorgan system failure ("MOSF"). The mechanism of SIRS is the excessive release of host derived inflammatory mediators, herein referred to as toxic mediators ("TM"). TM include various cytokines (tumor necrosis factor, TNF; the interleukins; interferon), various prostaglandins, various clotting factors (platelet activating factor, PAF), various peptidases, reactive oxygen metabolites, and various poorly understood peptides which cause organ dysfunction (myocardial depressant factor, MDF). If the inflammatory response is excessive, then injury or destruction to vital organ tissue may result in multiorgan dysfunction syndrome ("MODS"), including acute kidney failure.

Sepsis may also be defined as a life-threatening organ dysfunction caused by a dysregulated host response to infection.' Septic shock is defined as lactate levels rising above 2 mmol L−1 without hypovolemia and initiation of vasopressor treatment to keep mean arterial pressure above 65 mmHg. Organ dysfunction is defined as an increase of two or more in the Sequential Organ Failure Assessment (SOFA) scoring system (GUI et al, Turk J Anaesthesiol Reanim. 2017 June; 45(3): 129-138). According to the qSOFA scoring system, if 2 of the 3 following clinical criteria are positive, sepsis is indicated: 1. Altered mental status (GCS score <15); 2. Systolic blood pressure <100 mmHg; 3. Respiratory rate >22/min.

The expression "sepsis" as is used herein, also applies to any condition which would satisfy the parameters for sepsis upon infection as set out before or the before-mentioned qSOFA screening criteria wherein an increase of two or more in the Sequential Organ Failure Assessment (SOFA) scoring system indicates sepsis, and/or the qSOFA clinical criteria. For clinical operationalization, organ dysfunction can preferably be represented by an increase in the Sequential Organ Failure Assessment (SOFA) score of 2 points or more, which is associated with an in-hospital mortality greater than 10%. Septic shock may be defined as a subset of sepsis in which particularly profound circulatory, cellular, and metabolic abnormalities are associated with a greater risk of mortality than with sepsis alone. Patients with septic shock can be clinically identified by a vasopressor requirement to maintain a mean arterial pressure of 65 mm Hg or greater and serum lactate level greater than 2 mmol/L (>18 mg/dL) in the absence of hypovolemia.

As used herein, the "sequential organ failure assessment score" or "SOFA score" is one score used to track a patients status during the stay in an intensive care unit (ICU). The SOFA score is a scoring system to determine the extent of a person's organ function or rate of failure. The score is based on six different scores, one each for the respiratory, cardiovascular, hepatic, coagulation, renal and neurological systems. Both the mean and highest SOFA scores being predictors of outcome. An increase in SOFA score during the first 24 to 48 hours in the ICU predicts a mortality rate of at least 50% up to 95%. Scores less than 9 give predictive mortality at 33% while above 14 can be close to or above 95%. The term "sepsis" also includes severe sepsis or septic shock based on the SEPSIS-2 definition. The term "sepsis" also includes subjects falling within the SEPSIS-3 definition. The term "sepsis" used herein relates to all possible stages in the development of sepsis.

It is therefore one object of the present invention to provide a device for the extracorporeal purification and treatment of blood which can be used for treating a patient suffering from sepsis, especially in acute conditions and where medication is not indicated or effective. It is another object of the present invention to provide a device for the extracorporeal purification and treatment of blood which can be used for treating a patient suffering from both organ failure, specifically from renal failure, and sepsis.

Acute Renal Failure (ARF) and Sepsis-Associated Acute Kidney Injury (SA-AKI):

Acute renal failure (ARF), also referred to interchangeably as acute renal injury (AKI), is the rapid loss of the renal filtration function, which is characterized by metabolic acidosis, high potassium levels and a body fluid imbalance. This condition is usually marked by a rise in the serum creatinine concentration or blood urea nitrogen (BUN) concentration. As used herein, the term "acute kidney injury (AKI)" or "acute renal failure" relates to an abrupt and persistent decline in renal function.

Diagnostic criteria are typically, without limitation, as follows: An increase in serum creatinine of >0.3 mg/dl (26.5 μmol/L) within 48 h; or an increase in serum creatinine to 1.5 times baseline, which is known or presumed to have occurred within 7 d; or urine output <0.5 ml/(kg·h) for 6-12 h. According to the severity, the condition is divided into stages 1, 2, and 3. The Kidney Disease: Improving Global Outcomes (KDIGO) group defines these stages as 1: Serum creatinine increased 1.5-1.9 times baseline or increase >26.4 umol/L (0.3 mg/dl) or urinary output <0.5 ml/kg/h during a 6 hour block, 2: Serum creatinine increased 2.0-2.9 times baseline or urinary output <0.5 ml/kg/h during two 6 hour blocks, and 3: Serum creatinine increased >3 times baseline or increased to >353 umol/L (4 mg/dl) or initiation of renal replacement therapy or urinary output <0.3 ml/kg/h during more than 24 hours or anuria for more than 12 hours. As used herein, the term "infection-associated renal disfunction" relates to any loss of renal function in a patient suffering from an infection.

Renal disfunction is known to occur since the 1970s in association with multiple infectious agents (Zech et al, Adv Nephrol Necker Hosp. 1971; 1:231-58.). Without limitation, renal lesions are known to occur in acute kidney disease after infection with Staphylococcus septicemia, leptospiral infections, and rickettsial infections. Gram-negative septicemia, probably via infectious shock, lead more readily to tubular renal lesions. Hemolytic septicemias are known to cause tubular necrosis. Pulmonary or urinary tract infections may also lead to renal disfunction in severe cases.

As used herein, the term "sepsis-associated acute kidney injury (SA-AKI)" relates to an AKI in patients with sepsis. Sepsis is the most common trigger of ARF. ARF occurs in approximately 19% of patients with moderate sepsis, 23% with severe sepsis, and 51% with septic shock when blood cultures are positive. Instead of a single mechanism being responsible for its etiology, sepsis is associated with an entire orchestra of cellular mechanisms, adaptive and maladaptive, which potentiate each other and ultimately give rise to clinical SA-AKI. The microcirculation is an important physiological compartment where these mechanisms come together and exert their integrated and deleterious action. These mechanisms include endothelial dysfunction, inflammation, coagulation disturbance, and adaptive cell responses to injury. This ultimately results in kidney failure, and a key event in the early dysfunction of the kidney during sepsis appears to be a bio-energetic stress of the tubular epithelial cells, in response to the amplified inflammatory signal that peritubular microvascular dysfunction generates.

The present invention therefore addresses both kidney failure and any pathological negative effects induced by, for example, LPS. Lipopolysaccharides (LPS) elicit multiple acute pathophysiological effects, especially during sepsis, such as fever, lethality, macrophage and B-lymphocyte activation. The present invention therefore provides an approach towards ameliorating the negative effect of LPS and simultaneously providing RRT.

BRIEF DESCRIPTION OF THE DRAWINGS

The invention is further described by the following figures. There are intended to represent a more detailed illustration of a number of preferred non-limiting embodiments or aspects of the invention without limiting the scope of the invention described herein.

FIG. 2A shows a standard curve for the absorbance (405 nm) of dephosphorylated pNPP used to determine the activity of AP on modified membranes. The measured activity of the membrane samples with immobilized AP is presented in the table in μmol of pNPP min-1 together with the weight of each sample. The activity was extrapolated to that of a whole dialyzer using the sample membrane weight and the membrane weight of an entire dialyzer.
  (B)
FIG. 2B shows the measured absorbance of a pNPP solution in reaction to AP immobilized on epoxy (ECR8209F) and NH2 (ECR8409F) beads. Absorbance development was measured over time after mixing resins and a commercial pNPP solution in a 1:4 ratio. Absorbance was corrected for the signal observed when unmodified resins did not contain AP.

EXAMPLES

Figure 1:
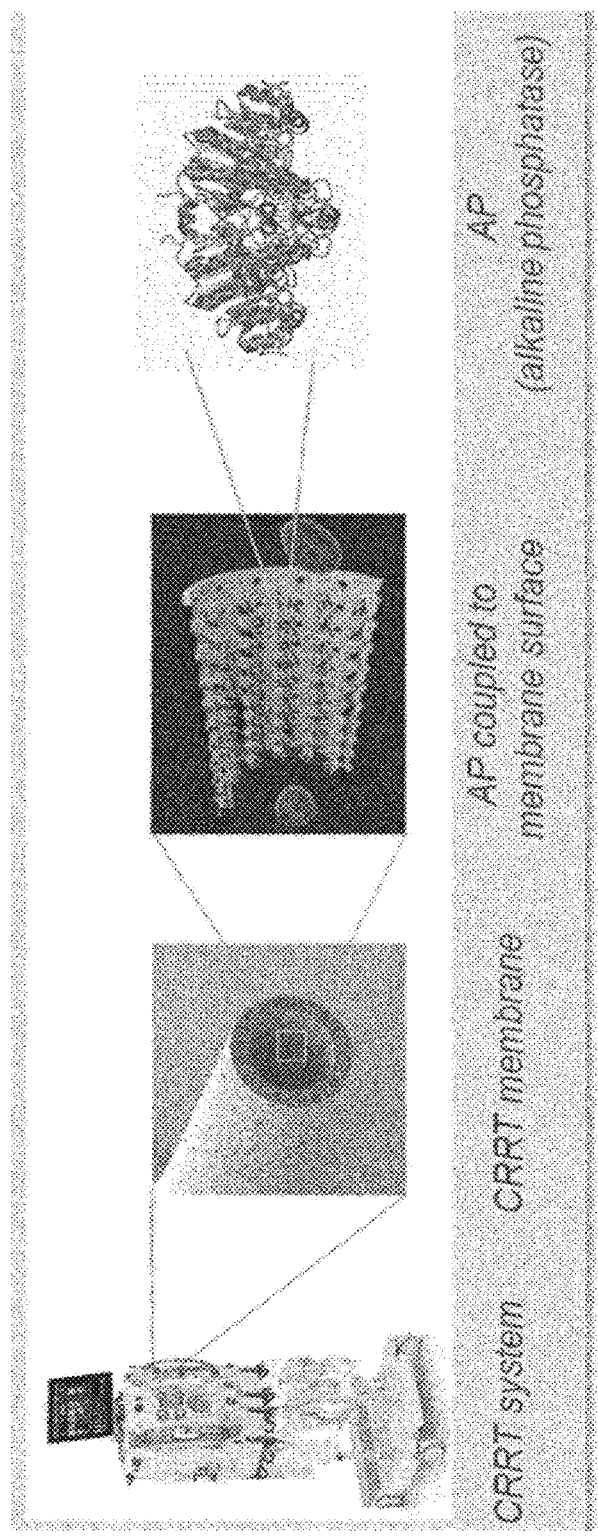
FIG. 1: Schematic representation of a preferred embodiment of the present invention indicating AP coupled to the lumen of a hollow dialysis membrane, attached in a blood treatment device assembled in an apparatus for an extracorporeal blood treatment circuit.

The invention is further described by the following examples. These are intended to present support for the workability of a number of preferred non-limiting embodiments or aspects of the invention without limiting the scope of the invention described herein.

Example 1: Immobilization of AP to Hemofilter Membranes

Membrane Preparation:

Alkaline Phosphatase (AP) was immobilized on various membranes in a proof of principle approach of the present invention. The table depicts the different components of the used membranes in percentage of the solution from which membranes are casted (in brackets the weight for a total solution weight of 50 g is given).

TABLE

| Membrane components | | |
|---|---|---|
| PES/PVP membranes | PES/PVP/Maleic Anhydride membranes | PES/PVP/chitosan membranes* |
| 80% (40.0 g) NMP | 78% (39.0 g) NMP | 74.57% (37.28 g) NMP |
| 12% (6.0 g) PES | 12% (6.0 g) PES | 13.24% (6.62 g) PES |
| 3% (1.5 g) PVP-K85 | 3% (1.5 g) PVP-K85 | 2.84% (1.42 g) PVP-K85 |
| 5% (2.5 g) $H_2O$ | 5% (2.5 g) $H_2O$ | 3.78% (1.89 g) $H_2O$ |
| | 2% (1.0 g) Poly(maleic anhydride-alt-1-octadecene) | 5.48% (2.74 g) Citric acid |
| | | 0.09% (0.05 g) Chitosan |

*Citric acid was first dissolved in $H_2O$ and chitosan was dissolved overnight, before addition of the rest of the mixture.

Components were dissolved overnight at 60° C. under continuous stirring. After completely dissolving all components, the solution was removed from the oil-bath and allowed to cool for 1 h. Flat-sheet membranes were casted using a 100 μm knife on an electronic casting machine. The knife was placed on a clean glass plate and approx. 10 mL of the polymer solution was applied. The motor was then engaged at 25 mm/s until the polymer film covered the entire glass plate. The motor was returned to its starting position, the knife removed, and the glass plated placed into a 500 mL bath of demineralized water. After 5 minutes, the water was replaced by fresh water, this process repeated after 2 hour and the membrane was left in the water bath for another 4 h, before being placed under vacuum at 60° C. overnight, to completely remove all NMP.

Alkaline Phosphatase Coupling to Membranes:

Membranes were cut into small pieces (approx. 1×1 cm) and their exact weight was determined (usually around 3-7 mg). A total of 5 mg of alkaline phosphatase (Santa Cruz Biotechnology) with an activity of 4000 U/mg and a protein content of 24.5 mg/mL was aliquoted into 5 µL aliquots, each containing 100 U/µL. For each immobilization experiment, a 5 µL aliquot was dissolved in 1 mL of 0.5M TRIS pH 8.5 containing 1 mM $CaCl_2$, to obtain a 500 U/mL solution. Membranes were placed in an Eppendorf containing 900 µL Millipore $H_2O$, 100 µL of 500 U/mL AP and 2.5 mg/mL of EDC. The membranes were then kept on a tumbler shaker at RT for 3-4 hours and placed at 4° C. overnight. After 18 h, the membranes were placed into a 50 mL 0.5M NaCl solution and left on a tumbler shaker in order to remove unbound AP. After 4 h, the wash solution was replaced with 1×PBS and left on the tumbler shaker for 2 more hours. Alternatively, membranes are placed in an Eppendorf containing 1 mL of MES buffer containing 2.5 mg/mL EDC for 30 minutes, removed and washed, and then placed into 1 mL of 50 U/mL AP overnight.

Activity Determination of Immobilized Alkaline Phosphatase:

After the final washing step, membranes were placed into 1 mL of p-Nitrophenyl phosphate (pNPP) Liquid substrate system (Sigma Aldrich). To determine the activity, 75 µL of the pNPP solution was removed and the absorbance was determined on t=10 min, 20 min, 30 min and 60 min. At each of these time points, the absorbance of the previous timepoint was determined again, and the change in absorbance over time was used to evaluate the release of Alkaline phosphatase from the membranes (since release results in continued color development and subsequent readings at later timepoints would show an increase in absorbance). The absorbance was then compared to the absorbance of standard concentrations of dephosporylated pNPP solution and the activity of the alkaline phosphatase on the membrane was determined in µmoles of pNPP converted per minute.

Figure 2:
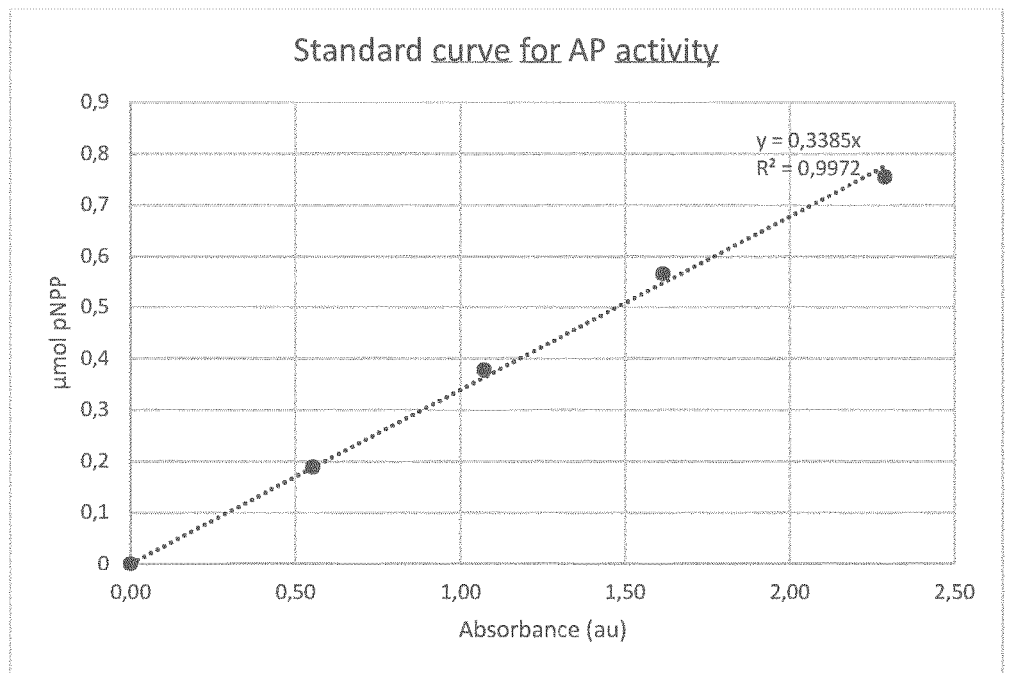
FIG. 2: Results from activity determination of immobilized Alkaline phosphatase.
  (A)
Figure 2:
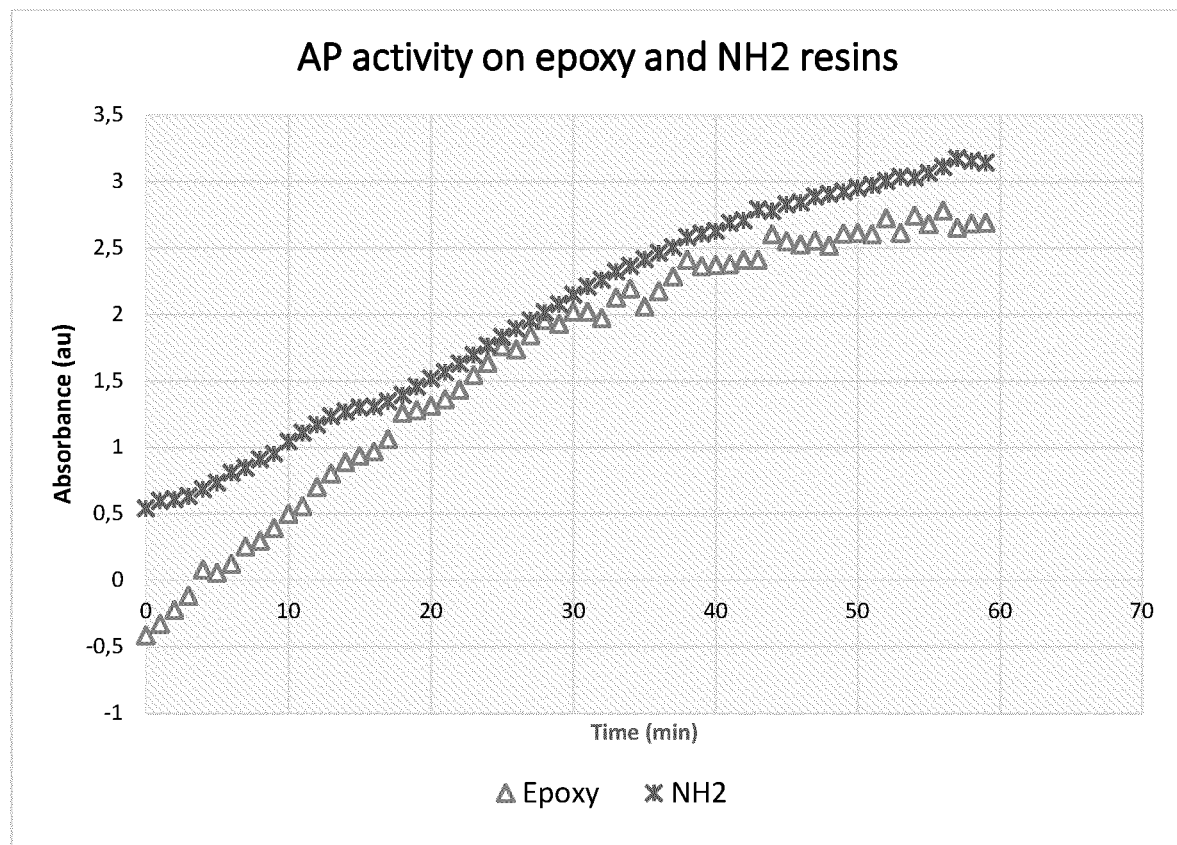
Figure 3:
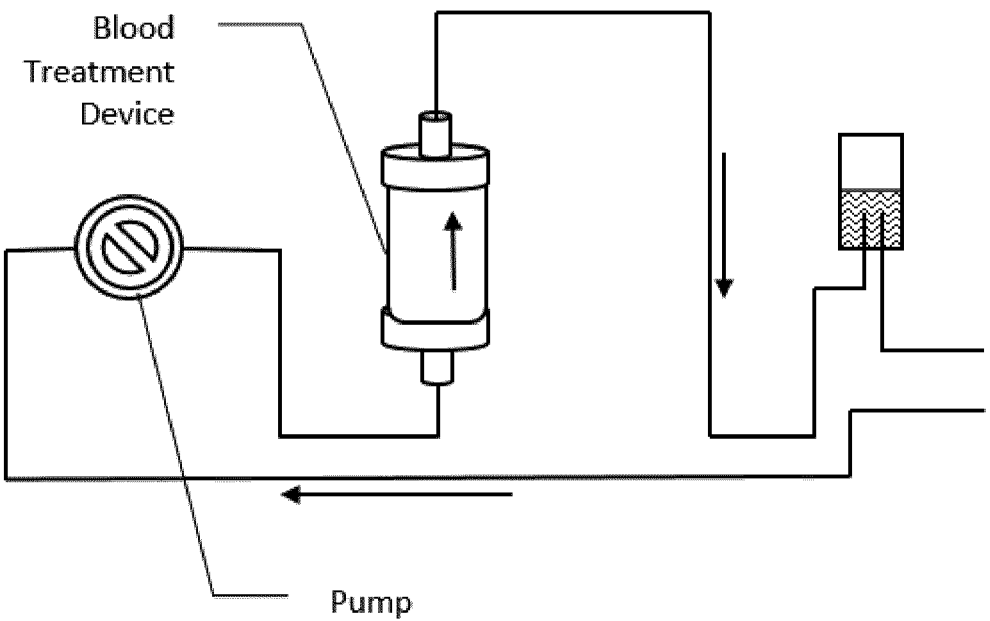
FIG. 3: Schematic representation of an extracorporeal treatment circuit comprising a blood treatment device. The device can be a cartridge or filter comprising a membrane, resin or nonwoven based support to which AP has been bound. The circuit can be operated in hemoperfusion mode. In cases where the blood treatment device is a hollow fiber membrane filter device the treatment mode can be hemodialysis, hemodiafiltration, hemofiltration or hemoperfusion of the filter with closed dialysate/filtrate ports.
Figure 4:
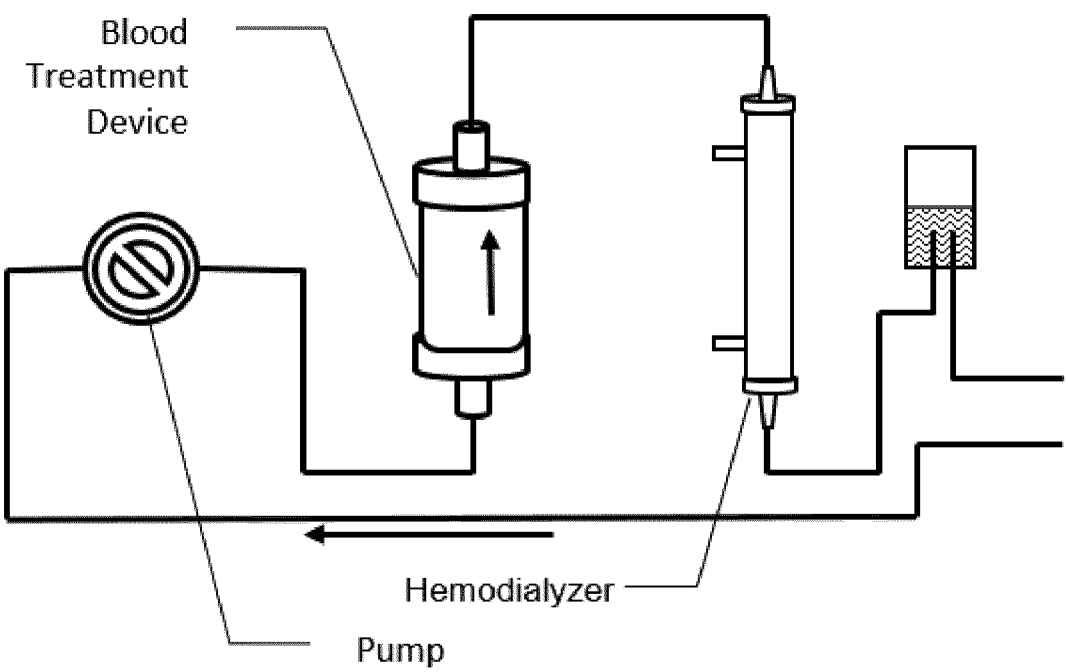
FIG. 4: Schematic representation of an extracorporeal treatment circuit comprising a blood treatment device. The device can be an adsorption cartridge comprising a resin or non-woven or a filter comprising a membrane, to which AP has been bound, respectively. The blood treatment device can be located upstream of a separate hemodialyzer (pre-dialyzer setting, FIG. 4A) or downstream of a hemodialyzer (post-dialyzer setting, FIG. 4B). The non-functionalized hemodialyzer in the circuit can be operated in different treatment modes depending on the medical need, including hemodialysis, hemodiafiltration or hemofiltration mode.
Figure 4:
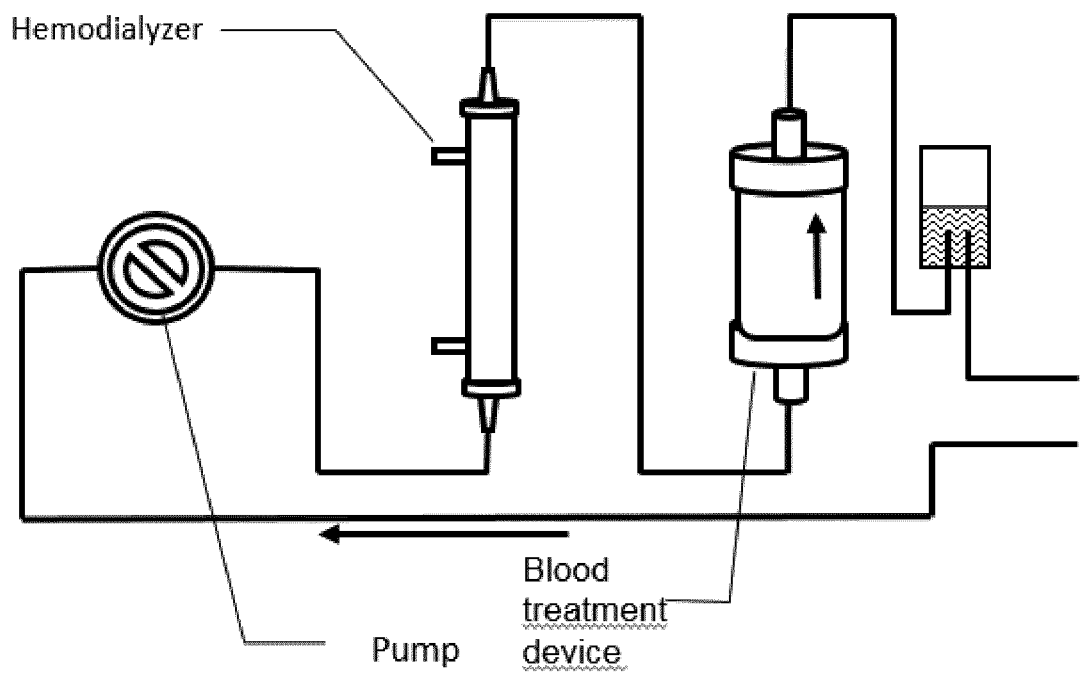
Figure 5:
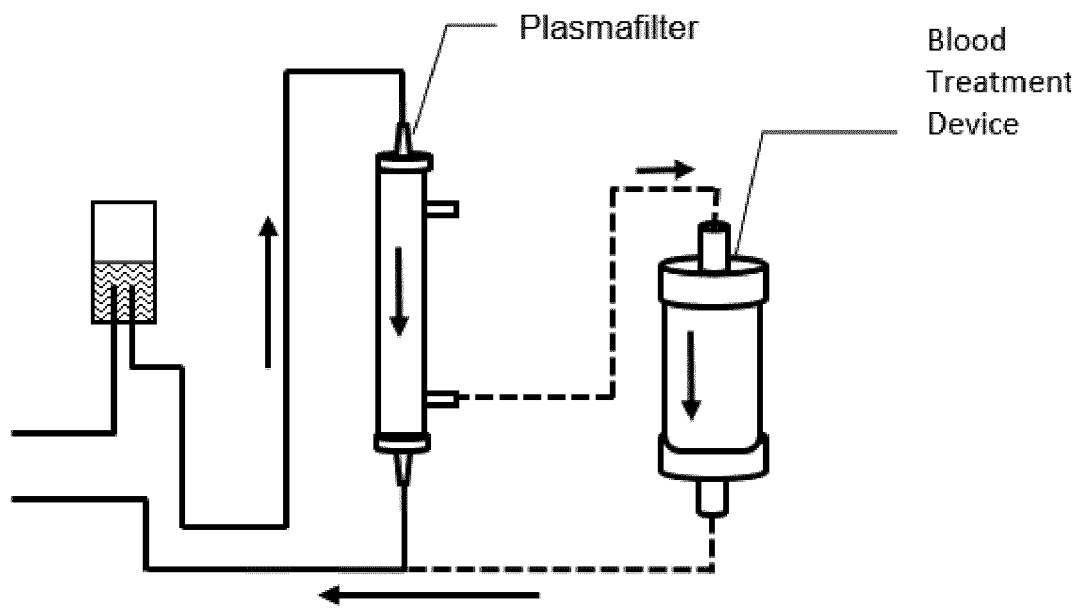
FIG. 5: Schematic representation of an extracorporeal treatment circuit comprising a blood treatment device. The device is perfused with blood plasma. In the embodiment shown, a plasma separation filter is used to separate blood plasma from whole blood. The plasma filter generates a plasma fraction comprising the target protein by means of pore sizes ranging from 0.03 μm and 2 μm. The plasma is perfused through the blood treatment device which comprises a matrix based on a non-woven, resin or membrane support to which AP has been bound.
Figure 6:
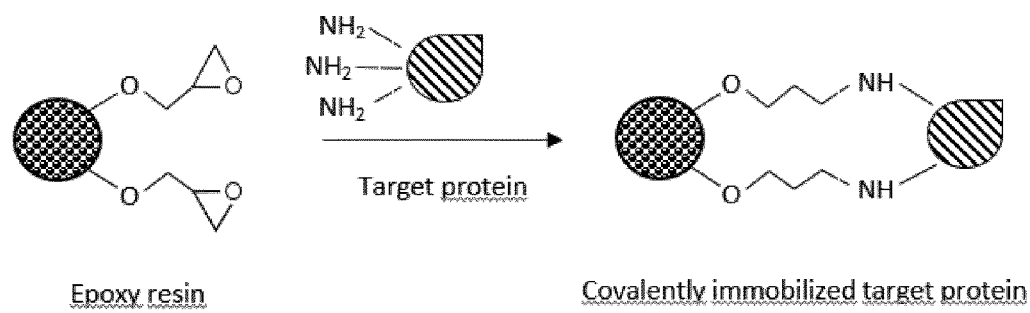
FIG. 6: Schematic representation of the covalent coupling of a target protein to an epoxy-activated or an amino support. The support can be a resin, a membrane, including hollow fiber membranes, flat sheet membranes or fiber mats, or a non-woven. (A) shows the direct coupling of the protein via amino groups of the protein to the support (Example 6). (B) shows the covalent immobilization of enzymes is based on the use of amino resins. Amino resins can be pre-activated with glutaraldehyde and then used in for covalent immobilization of enzymes. Reaction of an aldehyde group with an amino group of the target proteins is fast and forms a Schiff base (imine), resulting in a stable multipoint covalent binding between enzyme and carrier. The imine double bonds can be further reduced with borohydrides.
Figure 6:
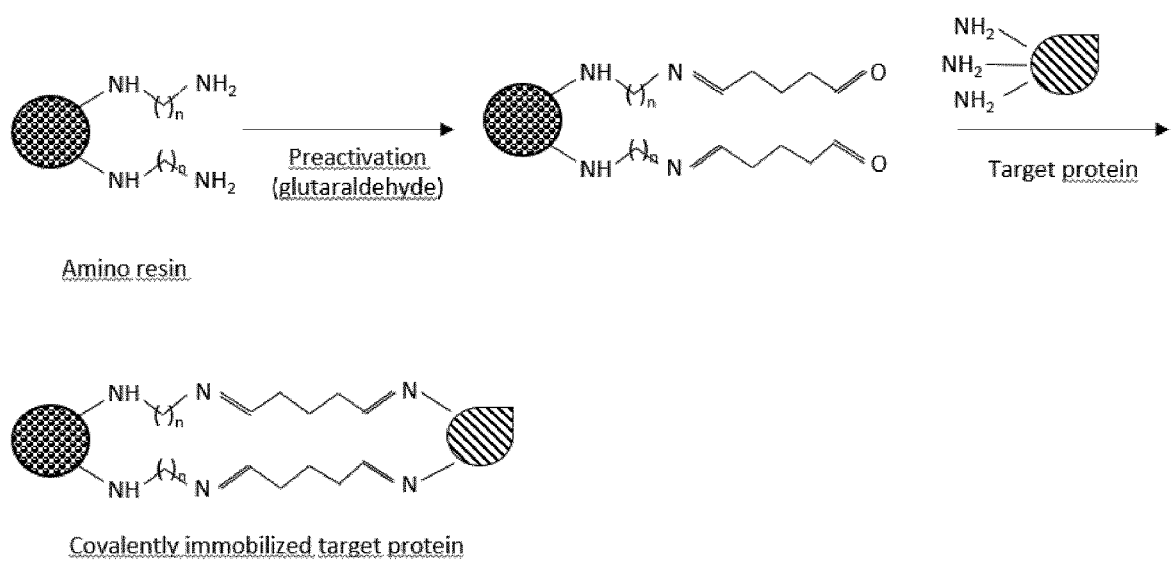

Results:

Results from two different membranes show the measured activity between 0.06 and 0.10 µmole $min^{-1}$. To clarify results and make up for different sample membrane weights, the activity was extrapolated to the activity for a whole dialyzer (containing 20 gram of membrane), indicating activities around 560 µmole $min^{-1}$. Release of alkaline phosphatase was in all cases minimal and, with one exception, did not exceed standard deviations of average activity. Results of these experiments are shown in FIG. 2A.

Example 2a: Immobilization of AP to an Epoxy-Functionalized Adsorber Resin

First, the resin is equilibrated. The resin is washed with immobilization buffer and filtered. A resin/buffer ratio of 1/1 (w/v) is preferable. The immobilization buffer is chosen to be compatible with AP. The process is repeated 2-4 times. The AP solution is prepared by dissolving the protein in immobilization buffer. For example, 100-200 mg AP can be loaded per gram of wet resin. Protein concentration can be determined by using standard protein content assays. The AP is dissolved in a sufficient amount of buffer to obtain a ratio resin/buffer of 1:4 (w/v). This ratio can be optimized depending on the protein used (range can vary from 1:1-1:4). Immobilization begins with the transfer of the immobilization buffer containing the AP protein into the immobilization vessel. The epoxy-functionalized resin, for example the Purolite® Lifetech™ resin described herein, is then added. The slurry is gently mixed at 70-80 rpm for 18 h and afterwards left without mixing for another 20 h. Magnetic stirring during protein immobilization should be avoided as this can damage the beads. Immobilization can be performed at temperatures of 20° C.-30° C., depending on the protein stability. Immobilizations should not be performed at high temperatures as this can cause degradation of the epoxy rings (hydrolysis) and facilitate microbial growth. Finally, the liquid phase is filtered off and collected. The protein content in the liquid is determined and the immobilization yield calculated. The resin is then washed with washing buffer. The process is repeated 2-4 times under gentle stirring or in column wash. An additional washing step using a 0.5 M NaCl containing buffer for complete desorption of non-covalently bound proteins can be performed. Excess water is removed by filtration. The immobilized AP protein can then be characterized in terms of moisture content and specific binding activity.

Example 2b: Immobilization of AP to an Amino-Functionalized Adsorber Resin

First, the resin is equilibrated. The resin is washed with immobilization buffer and filtered. A resin/buffer ratio of 1:1 (w/v) is preferable. The immobilization buffer is chosen to be compatible with the AP protein. In a second step 2% glutaraldehyde buffer is prepared starting from a solution of 25% (w/v) glutaraldehyde. A 2% glutaraldehyde (v/v) solution is prepared using the immobilization buffer. In a third step, the amino resin is activated by adding the 2% glutaraldehyde buffer prepared in step 2 to the resin. The optimal volume of 2% glutaraldehyde buffer should be in the range of resin/buffer ratio of 1:4 (w/v). The slurry is left to mix for 60 min at 20° C.-25° C. The beads are then filtered and washed with immobilization buffer using a resin/buffer ratio of 1:4 (w/v). It should be avoided to store pre-activated resin for a period longer than 48 h. Beads are then ready for the immobilization step. In a fourth step the AP protein solution is prepared. To that end, the protein is dissolved in immobilization buffer. For example, between 1 mg and 100 mg AP protein can be loaded per gram of wet resin. The protein concentration can be determined by using standard protein content assays.

The protein is dissolved in buffer to obtain a ratio resin/buffer of 1:4 (w/v). Optimization of this ratio can be pursued in further trials (range can vary from 1:1-1:4). In a fifth step, the protein is immobilized. The immobilization buffer is transferred into the immobilization vessel and the pre-activated amino resin (e.g. from Purolite®, Lifetech™) as prepared in step 3 is added. The slurry is gently mixed for 18 h at 70-80 rpm. Magnetic stirring should be avoided during immobilization as this can damage the beads. The immobilization can be performed at 20° C.-30° C. accordingly to AP protein stability. The immobilization should not be performed at high temperatures since this might cause side reactions of the aldehyde groups on the resin formed during step 3. Finally, the liquid phase is filtered off and collected. The protein content in the liquid is determined and the immobilization yield calculated. The resin is then washed with washing buffer. The process is repeated 2-4 times under gentle stirring or in column wash. An additional washing step using a 0.5 M NaCl containing buffer for complete desorption of non-covalently bound proteins can be performed. Excess water is removed by filtration. The immobilized AP protein can then be characterized in terms of moisture content and specific enzymatic activity.

Activity Determination of Immobilized Alkaline Phosphatase:

Both epoxy and amino-functionalized resins treated as described above to immobilize AP were subsequently placed into 1 mL of p-Nitrophenyl phosphate (pNPP) Liquid substrate system (Sigma Aldrich).

As described above, to determine the activity, 75 µL of the pNPP solution was removed and the absorbance was determined over time. The absorbance was then corrected for any background signal obtained when unmodified resins had not been treated with AP.

Results

Results from both epoxy and amino-functionalized resins show that AP is effectively immobilized and active based on the commercial pNPP solution used in the assay. Results of these experiments are shown in FIG. 2B.

Example 3: Immobilization of AP to Membranes Under Varying pH Conditions

Polyacrylonitrile AN69 membranes were employed to determine optimized pH conditions for AP binding to a membrane, verified by subsequent AP activity tests. The tests on pH optimization were carried out with "M-Filter" membranes (MF150), which are prepared as "minimodules", namely small filters commonly used for testing membrane characteristics. The tests described were carried out on AN69 minimodules each comprising a bundle of fibers, whereby in each bundle approx. 40 hollow fibers are present.

Figure 7:
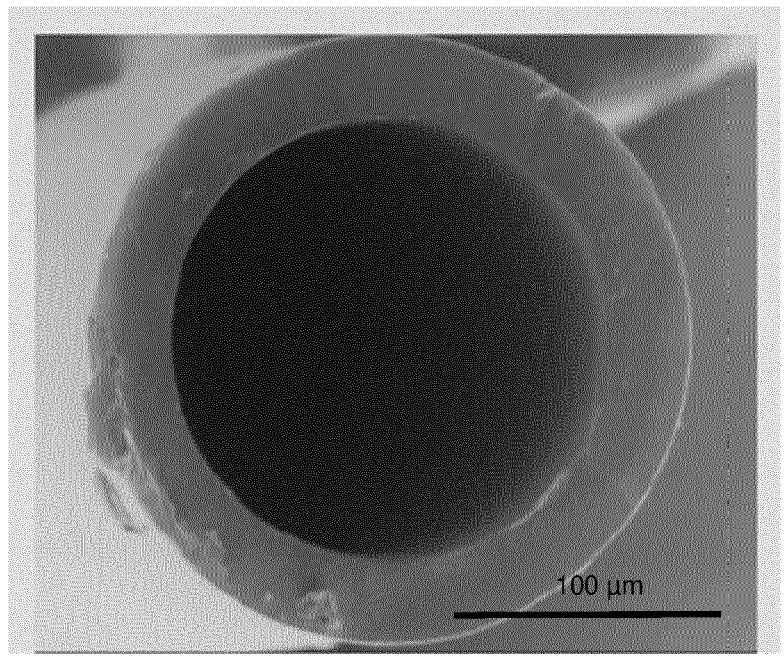
FIG. 7: A scanning electron microscope (SEM) image of an AN69 hollow fiber is shown together with a schematic setup of how such hollow fibers, when used in bundles, are employed in dialysis.
Figure 7:
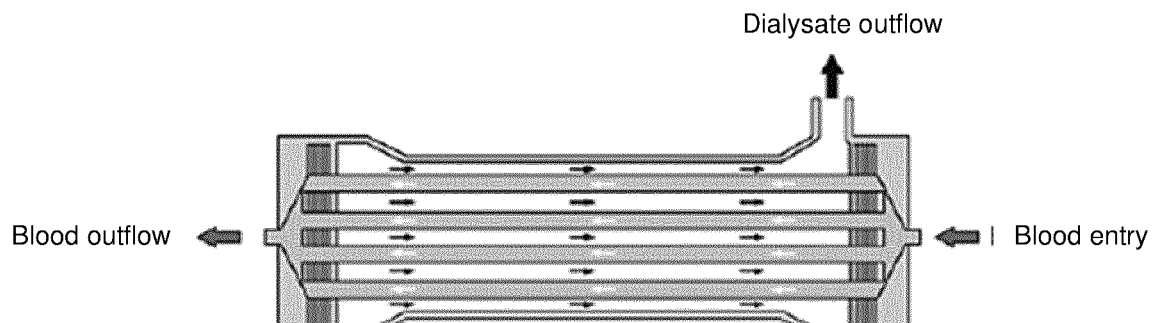
Figure 7:
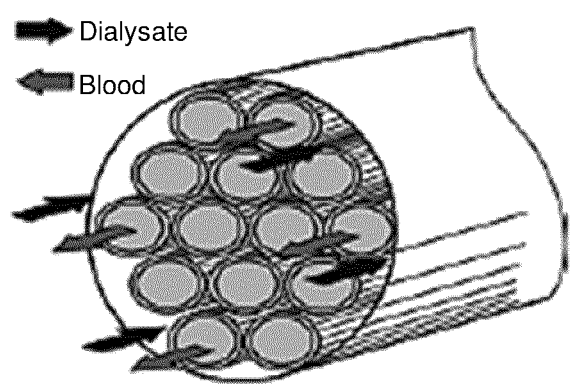

AN69 is an established polymer used in dialysis applications and is a copolymer of acrylonitrile and sodium methyl allyl sulfonate. The sulfonate groups result in a hydrophilic membrane with negative charges, which forms a hydrogel structure through water retention. This composition of the membranes allows for medium-sized proteins to be adsorbed. A scanning electron microscope (SEM) image of an AN69 hollow fiber is shown in FIG. 7 together with a schematic setup of how such bundles are employed in dialysis. The AN69 minimodules have an inner surface of approximately 1 $cm^2$ per fiber. This corresponds to an inner surface of 40 $cm^2$ per minimodule.

The minimodules were attached to a pumping station using common hosing (Promedt), through which liquid could be pumped (pump from Ismatec) at controlled rates through the minimodules.

In order to prepare the immobilized AP on the AN69 minimodules, the minimodules were coated with polyether imide (PEI) prior to attaching glutaraldehyde (GA) and AP. Due to the negative charges present on the AN69 membrane, a positively charged polymer can be attached through ionic interactions. In the present case PEI was employed, which carries positively charged amino groups. The PEI attachment is typically carried out in an acidic medium, as a result of which the amino groups are protonated, and the charge density is increased. By using citric acid in this process, a larger amount of PEI can be bound on the membrane than in alkaline medium. Optimization of the PEI treatment is discussed in more detail below.

After PEI treatment the AN69 membrane was treated with glutaraldehyde (GA) prior to immobilizing AP. Glutaraldehyde serves as a bifunctional spacer, generating a pre-activated polymer surface to bind the enzyme. Following the pre-activation of the surface, the free aldehyde groups of the glutaraldehyde are available in order to be able to bind another component via the same reaction. In the present case, AP is subsequently covalently bound in a second modification step via the free amino groups.

The AN69 minimodules were therefore:

Flushed to remove glycerin (with reverse osmosis water, 5 mL per minimodule at 1.5 mL/min, followed by 5 to 20 mL at 3 mL/min). Volume visually adjusted in order to remove air, Treated with PEI (PEI at 200 mg/kg in citric acid solution at 200 mg/kg, using 20 mL per minimodule at 3 mL/min), Flushed (in PBS, 20 mL per minimodule at 3 mL/min)

Treated with glutaraldehyde (2.5% GA solution, 40 mL per minimodule at 1.5 mL/min), Flushed (in PBS, 50 mL per minimodule at 1.5 mL/min), Treated with AP (1000 U AP per minimodule in PBS, 20 mL recirculated at 1.5 mL/min for 16 h), and Finally rinsed (in PBS, 50 mL per minimodule at 1.5 mL/min).

As a read-out, the immobilized AP activity was assessed. A test solution comprising pNPP substrate (para-nitrophenylphosphate disodium salt hexahydrate) with a matrix of magnesium chloride and zinc chloride in PBS buffer was used. To quantify the AP activity on the membrane, a single fiber was cut out of the minimodules. The modules were opened, the fibers were washed with PBS and then each fiber was placed in a plate well. The fibers were cut into appropriately sized pieces and pNPP test solution was applied. Readings were taken at 60 min and 120 min. As usual, the samples were measured against standard solutions of the free enzyme and therefore the results expressed as an activity of free AP under ideal standard (alkaline) conditions.

In order to assess optimal pH conditions for AP immobilization, two processes were modified, namely (1) coating of the membrane with glutaraldehyde (designated below as "GA-pH") and (2) subsequent immobilization of AP (designated below as "AP-pH"). For each of these treatments, multiple pH values of the relevant solutions were tested.

In the table below, the results from several protocols (I-IV) and the results for AP activity in U/$cm^2$ after 60 and 120 minutes are shown. In order to simplify the discussion, the corresponding average values are calculated and also displayed.

| Experiment # | Module # | GA-pH | AP-pH | Activity/U/$cm^2$ | | |
|---|---|---|---|---|---|---|
| | | | | t = 60 Min | t = 120 Min | Avg. |
| I | 73 | 7.4 | 7.4 | 0.09 | 0.10 | 0.10 |
| | 74 | | | 0.04 | 0.04 | 0.04 |
| | 75 | | | 0.15 | 0.18 | 0.16 |
| | 76 | | | 0.13 | 0.13 | 0.13 |
| II | 77 | | 9.9 | 0.41 | 0.41 | 0.41 |
| | 78 | | | 0.43 | 0.38 | 0.40 |
| | 79 | | | 0.44 | 0.40 | 0.42 |
| | 80 | | | 0.39 | 0.36 | 0.37 |
| III | 81 | 9.9 | 7.4 | 0.10 | 0.14 | 0.12 |
| | 82 | | | 0.15 | 0.20 | 0.18 |
| | 83 | | | 0.13 | 0.17 | 0.15 |
| | 84 | | | 0.73 | 0.92 | 0.82 |

-continued

| Experiment # | Module # | GA-pH | AP-pH | Activity/U/cm² | | |
|---|---|---|---|---|---|---|
| | | | | t = 60 Min | t = 120 Min | Avg. |
| IV | 85 | | 9.9 | 0.14 | 0.16 | 0.15 |
| | 86 | | | 0.16 | 0.15 | 0.16 |
| | 87 | | | 0.68 | 0.73 | 0.70 |
| | 88 | | | 0.80 | 0.82 | 0.81 |

The experiments under II gave reproducibly high AP activities in the range of from 0.38 to 0.45 U/cm², which is about ten-fold higher than the lowest limit which was empirically estimated as a therapeutically relevant activity (0.05 U/cm²). Alternative pH conditions also appear effective, although less reproducible than in experiment II.

Example 4: Immobilization of AP to Beads Under Varying pH Conditions

Experiments similar to Example 3 above were conducted using amino-functionalised beads (Purolite Lifetech ECR 8408F) as a matrix for immobilization of the AP. Beads were pre-treated using GA at varying pH values and subsequently treated with AP, also at different pH values.

Experiments were conducted in 96-well plates with GA/AP-treated beads in 900 μL of pNPP solution under constant stirring. 75 μL of reaction was removed and analyzed in a separate 96-well plate at 10, 30, 60 and 120 minutes, using the photometric activity measurement described above.

The table below outlines the AP activity determined after 10 minutes using the beads as a solid matrix.

| Experiment | Extinction | Activity in U/mL |
|---|---|---|
| Reference-Beads (washed) | 0.27875 | 0.05 |
| Beads + GA pH 7.4 + AP pH 7.4 | 0.3505 | 0.62 |
| Beads + GA pH 7.4 + AP pH 9.9 | 0.8356 | 4.51 |
| Beads + GA pH 9.9 + AP pH 9.9 | 0.8938 | 4.98 |
| Beads + GA pH 9.9 + AP pH 7.4 | 0.41765 | 1.16 |
| Beads + AP pH 7.4 | 0.28655 | 0.11 |
| Beads + AP pH 9.9 | 0.26645 | −0.05 |

As can be observed from the above results, AP activity was maintained after coupling to the beads, the most effective immobilization conditions being GA pH 9.9+AP pH 9.9 or GA pH 9.9+AP pH 7.4, similar to the AN69 minimodule experiments above. The GA step is important when using these beads (homobifunctional spacer glutadialdehyde), as no enzyme binding respectively activity can be observed by bringing the beads directly together with the AP.

Example 5: Adjustment of Cofactors for AP Activity

The AP used in the above examples was commercially available and shipped with cofactor concentrations of 1 mM $MgCl_2$ and 0.1 mM $ZnCl_2$. In the activity test for AP described above, cofactor concentrations are 0.5 mM $MgCl_2$ and 0.1 mM $ZnCl_2$. In the PBS simulated use tests, cofactors $Mg^{2+}$ and $Zn^{2+}$ are also added in a concentration of 0.5 mmol/L and 0.1 mmol/L, respectively (see below for simulated use stability tests).

Further experiments were conducted using the AN69 membrane minimodules from Example 3, in order to titrate $Mg^{2+}$ concentration in dilution series from 5 mM to 0.005 mM. Although some slowing down of AP reaction was observed, clear differences between the kinetic profiles of different magnesium concentrations could not be observed, indicating that the immobilized AP is likely to exhibit suitable activity at the cofactor concentration found in human blood samples.

Blood plasma concentration in healthy individuals is similar to serum, ranging from 0.7 to 1.0 mM. Accordingly, when the device is in clinical use, blood would have high enough levels of magnesium to support AP activity. The same is true for zinc. Serum zinc concentrations are 12.4±1.4 μmol/L (9-22 μmol/L in women; 12-26 μmol/L in men).

This example also demonstrates that a device for extracorporeal therapy containing immobilized AP, may preferably be filled with or stored in a buffer or other solution, wherein the matrix comprising the immobilized AP is immersed in said buffer or solution, with the presence of $Mg^{2+}$ in a concentration of 0.1 to 2, preferably 0.1 to 1 mmol/L, and a $Zn^{2+}$ in a concentration of 5 to 150, preferably 10 to 100 μmol/L.

Example 6: Optimizing PEI Density on Membranes

Optimal PEI coating and density was tested using the "TNBS"-Test for APA-CRRT. The TNBS test is known to a skilled person (based on 2,4,6-Trinitrobenzene sulfonic acid) and can be used for quantitative analysis of amino functions e.g. on the membrane surface. TNBS reacts with reactive amines molecules to from a highly chromogenic (orange) product, whose absorbance at 335 to 345 nm can be measured with a plate reader or spectrophotometer. The amino function is derived from the PEI in the present examples.

A 50 g/L TNBS solution was used for the test. The absorbance of the solution was measured at 340 nm on a photometer blanked against reverse osmosis water. In 15 mL of the 0.1 g/L TNBS solution, all 40 fibers from one minimodules are removed and added to the solution in approximately 1 cm long pieces. After shaking for 30 minutes at room temperature in the dark, the supernatant of the respective solution was removed, and the absorbance measured. The decrease in absorbance correlates directly with the number of reactive amines. An optimal PEI density on the membrane of 1-3 μmol/g of hollow fiber membrane was achieved.

It was found that membranes which are coated with the process as described in Example 3 can be AP-functionalized very efficiently. The PEI coating process based on citric acid (see Example 3; preferably PEI at 200 mg/kg in citric acid solution at 200 mg/kg) is effective. Further experiments were also conducted using functionalization with PEI/GA/AP based on a pre-coated (PEI-coated) ST-Filter, which is the same AN69 membrane, but pre-coated with PEI in commercial production. AP immobilization to pre-treated PEI membranes was also successful. However, those hollow fibers with AP showed significantly lower enzymatic activity as the ones mentioned above.

Example 7: Simulated Use and Stability of AP Activity in PBS and Human Plasma

In order to assess whether immobilized AP is stable over time, the following experiments were conducted. Minimodules were prepared as described above under Experiment II of Example 3, and then attached to a pumping station, as in Example 3.

In all experiments, the minimodules were closed on the dialysate side and perfused recirculating on the lumen side with the appropriate medium. The flows and volumes were set accordingly in order to simulate a 72-hour dialysis, which corresponds to a maximum permitted use time of a standard dialysis filter for acute treatment.

With standard dialysis, flows of about 200 mL/min-500 mL/min are used with a blood volume of about 5 L. The inner surface of a dialyzer used here is, for example, 1.5 m$^2$. For a minimodule with an area of 40 cm$^2$, this results in a flow of 0.5 mL/min-1.3 mL/min and a pool volume of 13 mL. Since the calculated values are too low for the laboratory test, the flow was set to 1.5 mL/min and the pool volume to 20 mL.

A PBS buffer with 0.5 mmol/L $MgCl_2$ and 0.1 mmol/L $ZnCl_2$ was used as the medium for the perfusion. The modules were then perfused under a warming hood at 37° C. for the specified period. At certain times, samples were taken from the pool and measured for activity in order to investigate possible leaching or washout processes. The fibers from the corresponding modules were then subjected to the activity test described above without further treatment.

Activity measurements showed an activity prior to 72 h perfusion of 0.4 U/cm$^2$, whereas the activity after the test was 0.7-2.0 U/cm$^2$. No activity was observed in the eluate pool, indicating that leaching or washing out of immobilized AP does not occur or is negligible.

When the minimodule with an AP-functionalized membrane is perfused with PBS in the presence of the AP cofactors, the immobilized activity is therefore reliably retained (or even reproducibly increased) over 72 h. It is assumed that the AP before perfusion is already somewhat depleted from cofactors, which the enzyme is subsequently provided through the buffer and therefore not only maintains but increases activity over time. In any case, the AP on the hollow fiber membrane is highly stable.

In human plasma, the effect is even more pronounced. The experiments were repeated using human plasma in place of PBS buffer. Human plasma, by nature, already contains the required cofactors of AP. Activity measurements showed an activity prior to 72 h perfusion in plasma of 0.4 U/cm$^2$, whereas the activity after the test was 1.6-2.4 U/cm$^2$. No activity was observed in the eluate pool, indicating that leaching or washing out of immobilized AP does not occur or is negligible.

Example 8: Stability of AP Activity After Sterilization

Sterilization techniques are required for clinical products to inactivate potential microorganismal pathogens. Due to the necessary AP activity, heat treatment is possible, but not preferred, as steam sterilization could damage the membrane and/or denature the enzyme.

Sterilization using gamma radiation was assessed as a promising approach. During gamma sterilization, gamma radiation is generated by a radioactive radiation source, which then reaches the product. Gamma rays have a high penetration depth and can therefore be used for the sterilization of products in the final packaging.

The gamma sterilization was carried out on minimodules as described above using a dose of approximately 30 kGy. With this sterilization method, the minimodules, still moistened by the modification processes (approx. 0.5 g moisture/ minimodule), can be closed with stoppers and do not need to be filled with glycerin. After the coating (as in Example 3), the minimodules on the blood and dialysate side were filled with reverse osmosis water and closed with stoppers and sent for gamma sterilization.

Figure 8:
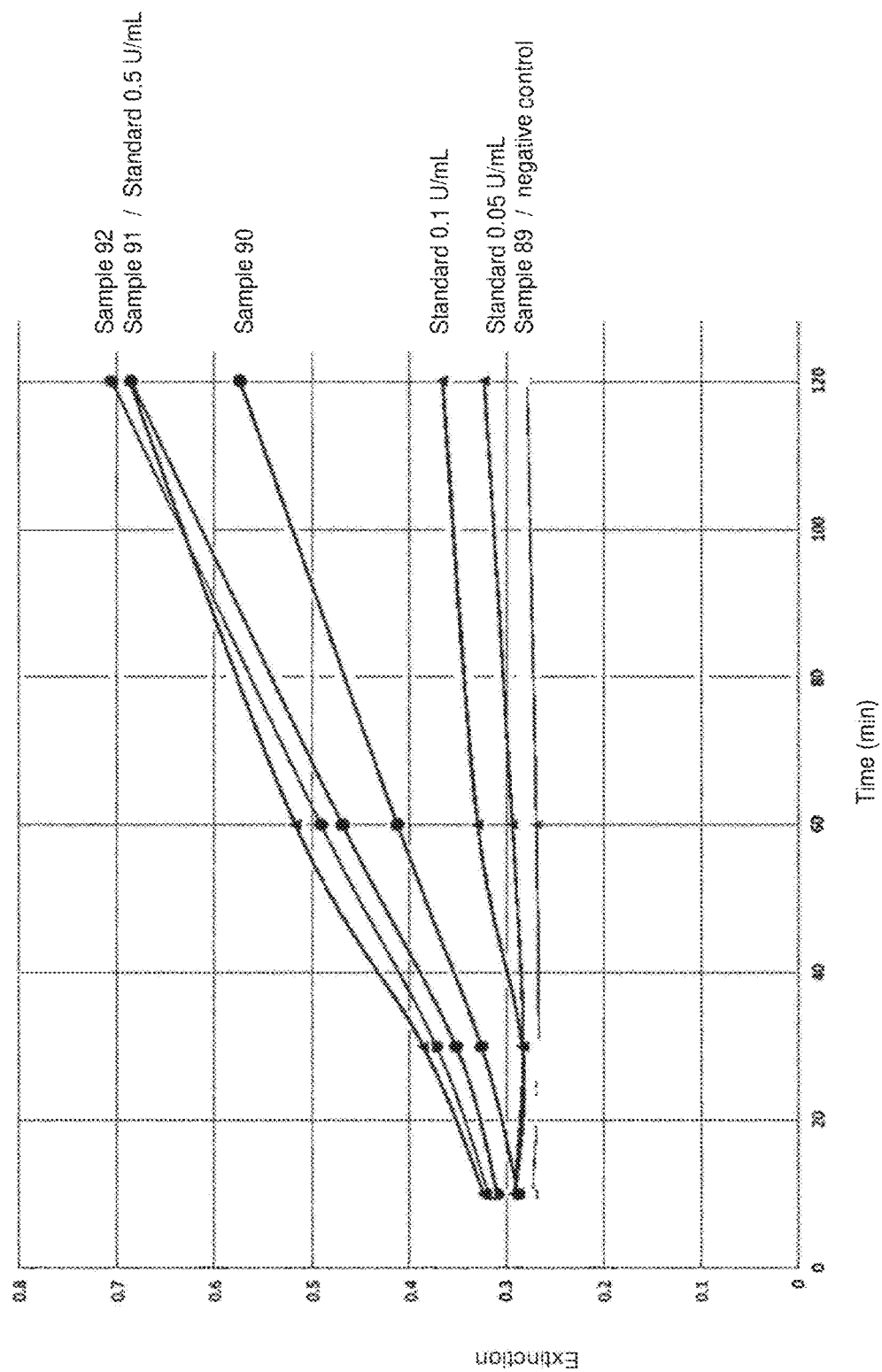
FIG. 8: Results of the AP activity test after gamma sterilization of minimodules.

After sterilization with a dose of 30.6 kGy, the water contained in the minimodules was collected and stored. The two minimodules 91 and 92 were pre-rinsed with the salt solution of $MgCl_2$ and $ZnCl_2$. For this purpose, the minimodules were connected to hose sets and filled with a flow of 3 mL/min. The hoses were then disconnected and the minimodules left to stand for 30 minutes, before being pumped empty and subjected to the activity test. The results are shown in FIG. 8.

The two minimodules 89 and 90 were directly subjected to the activity test, as described above. The two flushed minimodules 91 and 92 showed an activity of about 0.5 U/cm$^2$. The non-flushed minimodule 89 showed a very low activity of 0.02 U/cm$^2$. Minimodule 90 showed a higher activity of about 0.3 U/cm$^2$. Minimodules modified with the same procedure and not sterilized showed an activity of about 0.4 U/cm$^2$. Sterilization of water-filled minimodules therefore shows little influence on 3 of the 4 minimodules when assessed for AP activity.

Alternatively, sterilization with ethylene oxide (EtO) gas was also carried out. The minimodules were first filled with glycerin, to prevent the gel membrane from drying out, and subsequently treated using standard techniques. Ethylene Oxide (EtO) is a common gas used for low temperature sterilization. It is a colorless, poisonous gas that attacks the cellular proteins and nucleic acids of microorganisms. It is most commonly used to sterilize medical instruments with long lumens and materials that have to be sterilized but cannot withstand higher temperature.

EtO sterilization was carried out on minimodules and the activity of AP was subsequently determined, as described above. EtO sterilization led to a slight reduction of AP activity. After testing 5 minimodules (two without and three with EtO sterilization), the AP activity was lost in only one minimodule (likely due to an unknown technical error). In the two minimodules that retained AP activity, initial data revealed that after 120 minutes in the activity test, 40% of AP activity was maintained after EtO sterilization, compared to unsterilized controls. These test results are preliminary and being repeated.

In summary, both gamma and EtO sterilization appear feasible in order to maintain AP activity immobilized on membranes.

The invention claimed is:

1. A blood treatment device configured to dephosphorylate one or more substances selected from the group consisting of extracellular adenosine triphosphate (ATP), adenosine diphosphate (ADP), adenosine monophosphate (AMP), lipopolysaccharide (LPS), and combinations thereof, in the blood of a patient in need thereof in an extracorporeal blood circuit, wherein the device comprises a matrix having alkaline phosphatase (AP) immobilized thereon.

2. A blood treatment device according to claim 1, wherein the blood treatment device is located in an extracorporeal blood circuit through which the blood of the patient passes, and which comprises means for transporting blood from the patient's vascular system to the blood treatment device at a defined flow rate and for returning the treated blood back to the patient.

3. A blood treatment device according to claim 1, wherein the blood treatment device is a hemofilter.

4. A blood treatment device according to claim 1, wherein the blood treatment device is an adsorber cartridge.

5. A blood treatment device according to claim 2, wherein the extracorporeal blood circuit circuit additionally comprises a hemofilter located upstream or downstream of an adsorber cartridge.

6. A blood treatment device according to claim 1, wherein the alkaline phosphatase (AP) is bovine intestinal alkaline AP.

7. A blood treatment device according to claim 1, wherein the alkaline phosphatase (AP) is a recombinant and/or chimeric form of AP.

8. A blood treatment device according to claim 1, wherein the blood treatment device is a hemofilter comprising a bundle of hollow fibers and the alkaline phosphatase (AP) is immobilized to at least the lumen of said hollow fibers of the bundle.

9. A blood treatment device according to claim 1, wherein the matrix to which the alkaline phosphatase (AP) is immobilized, comprises:
 a copolymer of acrylonitrile and sodium methallyl sulfonate, or
 a combination of i) a polysulfone, poly(ether)sulfone (PES), polyaryl(ether)sulfone (PAES), and any combination thereof and ii) polyvinylpyrrolidone (PVP), or
 a combination of i) a polysulfone, PES PAES, and any combination thereof and ii) PVP, with an additive selected from chitosan, maleic anhydride-alt-1-octadecene, and combinations thereof.

10. A blood treatment device according to claim 9, wherein the alkaline phosphatase (AP) is immobilized to the matrix—
 via an ester linkage resulting from a reaction between an OH group of i) a polysulfone, poly(ether)sulfone (PES), polyaryl(ether)sulfone (PAES), and any combination thereof and ii) a COOH group of AP, or
 via a peptide linkage resulting from a reaction between an NH$_2$ group present on the matrix and a COOH group of AP, or
 via a peptide linkage resulting from a reaction between a COOH group created by maleic anhydride-alt-1-octadecene and an NH2 group of AP.

11. A method for manufacturing a blood treatment device according to claim 1, wherein said device is configured to dephosphorylate one or more substances selected from the group consisting of extracellular adenosine triphosphate (ATP), adenosine diphosphate (ADP), adenosine monophosphate (AMP), lipopolysaccharide (LPS), and combinations thereof, in the blood of a patient in need thereof, comprising immobilizing alkaline phosphatase (AP) to a matrix.

12. A method for manufacturing a blood treatment device according to claim 11, wherein the blood treatment device is a hemofilter comprising a bundle of hollow fiber membranes and the alkaline phosphatase (AP) is immobilized to at least the lumen of said hollow fibers of the bundle.

13. A method for manufacturing a blood treatment device according to claim 11, wherein the alkaline phosphatase (AP) is covalently bound to the matrix, the method comprising treatment of said matrix and/or AP using a carbodiimide compound.

14. A method for treating an infection in a patient, said method comprising the step of administering the blood treatment device according to claim 1 to the patient, wherein the blood treatment device transports blood from the vascular system of the patient to the blood treatment device and returns treated blood from the blood treatment device to the patient.

15. The method of claim 14, wherein the infection is sepsis or septic shock.

16. The method of claim 14, wherein the infection is an infection associated with renal dysfunction.

17. The method of claim 16, wherein the infection associated with renal dysfunction is sepsis-associated acute kidney injury (AKI).

18. The method of claim 14, wherein said method comprises continuous renal replacement therapy in an acute setting.

19. The method of claim 14, wherein the method comprises the step of extracorporeally dephosphorylating one or more substances selected from the group consisting of extracellular adenosine triphosphate (ATP), adenosine diphosphate (ADP), adenosine monophosphate (AMP), lipopolysaccharide (LPS), and combinations thereof, in the blood of a patient and then returning the treated blood back to the patient.

20. The method of claim 14, wherein the infection is a blood infection or a systemic infection.

* * * * *